US009790280B2

(12) United States Patent
Rue et al.

(10) Patent No.: US 9,790,280 B2
(45) Date of Patent: Oct. 17, 2017

(54) MONOCLONAL CANINE CD20 ANTIBODIES AND METHODS OF USE

(71) Applicant: Elanco Tiergesundheit AG, Indianapolis, IN (US)

(72) Inventors: Sarah Rue, San Diego, CA (US); Brendan Eckelman, San Diego, CA (US); Quinn Deveraux, San Diego, CA (US); Marc Nasoff, San Diego, CA (US)

(73) Assignee: Elanco Tiergesundheit AG, Indianapolis, IN (US)

( * ) Notice: Subject to any disclaimer, the term of this patent is extended or adjusted under 35 U.S.C. 154(b) by 307 days.

(21) Appl. No.: 14/354,280

(22) PCT Filed: Oct. 25, 2012

(86) PCT No.: PCT/US2012/061782
§ 371 (c)(1),
(2) Date: Apr. 25, 2014

(87) PCT Pub. No.: WO2013/063186
PCT Pub. Date: May 2, 2013

(65) Prior Publication Data
US 2015/0125453 A1    May 7, 2015

Related U.S. Application Data

(60) Provisional application No. 61/551,918, filed on Oct. 26, 2011, provisional application No. 61/699,300, filed on Sep. 11, 2012.

(51) Int. Cl.
| | |
|---|---|
| *C07K 16/30* | (2006.01) |
| *C07K 16/28* | (2006.01) |
| *A61K 39/395* | (2006.01) |
| *G01N 33/574* | (2006.01) |
| *A61K 45/06* | (2006.01) |

(52) U.S. Cl.
CPC ...... *C07K 16/2887* (2013.01); *A61K 39/3955* (2013.01); *A61K 39/39558* (2013.01); *A61K 45/06* (2013.01); *C07K 16/2896* (2013.01); *C07K 16/3061* (2013.01); *G01N 33/57426* (2013.01); *C07K 2317/20* (2013.01); *C07K 2317/24* (2013.01); *C07K 2317/33* (2013.01); *C07K 2317/52* (2013.01); *C07K 2317/56* (2013.01); *C07K 2317/92* (2013.01)

(58) Field of Classification Search
None
See application file for complete search history.

(56) References Cited

U.S. PATENT DOCUMENTS

| | | |
|---|---|---|
| 5,225,539 A | 7/1993 | Winter |
| 5,593,861 A | 1/1997 | Maeda et al. |
| 5,658,570 A | 8/1997 | Newman et al. |
| 5,677,180 A | 10/1997 | Robinson et al. |
| 5,681,722 A | 10/1997 | Newman et al. |
| 5,693,780 A | 12/1997 | Newman et al. |
| 5,714,350 A | 2/1998 | Co et al. |
| 5,736,137 A | 4/1998 | Anderson et al. |
| 5,750,105 A | 5/1998 | Newman et al. |
| 5,843,439 A | 12/1998 | Anderson et al. |
| 6,306,393 B1 | 10/2001 | Goldenberg |
| 6,455,043 B1 | 9/2002 | Grillo-Lopez |
| 2002/0041847 A1 | 4/2002 | Goldenberg |
| 2002/0150580 A1 | 10/2002 | Newman et al. |
| 2003/0054497 A1 | 3/2003 | Co et al. |
| 2003/0219433 A1 | 11/2003 | Hansen et al. |
| 2004/0167319 A1 | 8/2004 | Teeling et al. |
| 2005/0255552 A1 | 11/2005 | Flynn et al. |
| 2005/0271662 A1 | 12/2005 | Beall |
| 2006/0121032 A1 | 6/2006 | Dahiyat et al. |
| 2006/0134098 A1 | 6/2006 | Bebbington et al. |
| 2007/0020259 A1 | 1/2007 | Hansen et al. |
| 2008/0045700 A1 | 2/2008 | Beall |
| 2008/0299546 A1 | 12/2008 | Kano et al. |
| 2010/0061988 A1 | 3/2010 | Hansen |
| 2011/0002917 A1 | 1/2011 | Hansen |
| 2011/0091483 A1 | 4/2011 | Beall |
| 2011/0217298 A1 | 9/2011 | Hansen |
| 2011/0217304 A1 | 9/2011 | Hansen |

OTHER PUBLICATIONS

MacCallum et al. "Antibody-antigen interactions: contact analysis and binding site topography", Journal of Molecular Biology, 1996. vol. 262, pp. 732-745.*

De Pascalis et al. "Grafting of abbreviated complementarity determining regions containing specificity determining residues essential for ligand contact to engineer a less immunogenic humanzied monoclonal antibody", Journal of Immunology, 2002. vol. 169, pp. 3076-3084.*

Kano et al., Canine CD20 gene, Veterinary Immunology and Immunopathology, 2005, pp. 265-268, v. 108.

Lim et al., Anti-CD20 monoclonal antibodies: historical and future perspectives, Haematologica, 2010, pp. 135-143, v. 95.

* cited by examiner

*Primary Examiner* — Ron Schwadron
(74) *Attorney, Agent, or Firm* — David L Pflugh

(57) ABSTRACT

This disclosure relates to immunogens and monoclonal antibodies useful in the identification and/or treatment of cancer cells, including those of the dog. In one example, chimeric anti-canine CD20 antibodies are provided. The antibodies can be used therapeutically to treat lymphoma in dogs.

7 Claims, 6 Drawing Sheets

SEQUENCE LISTING

```
<160> NUMBER OF SEQ ID NOS: 83

<210> SEQ ID NO 1
<211> LENGTH: 9
<212> TYPE: PRT
<213> ORGANISM: Canis familiaris

<400> SEQUENCE: 1

Leu Ile Lys Ala Pro Met Pro Tyr Val
1               5

<210> SEQ ID NO 2
<211> LENGTH: 6
<212> TYPE: PRT
<213> ORGANISM: Canis familiaris

<400> SEQUENCE: 2

Asp Ile His Asn Cys Asp
1               5

<210> SEQ ID NO 3
<211> LENGTH: 112
<212> TYPE: PRT
<213> ORGANISM: Mus musculus

<400> SEQUENCE: 3

Asp Val Val Met Thr Gln Asn Pro Leu Ser Leu Pro Val Ser Leu Gly
1               5                   10                  15

Asp Gln Ala Ser Ile Ser Cys Arg Ser Ser Gln Ser Leu Ile Tyr Asn
            20                  25                  30
```

```
Asn Gly Asn Thr Tyr Leu His Trp Tyr Arg Gln Lys Pro Gly Gln Ser
            35                  40                  45

Pro Lys Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65              70                  75                  80

Ser Arg Val Glu Ala Glu Asp Leu Gly Val Tyr Phe Cys Ser Gln Ser
                 85                  90                  95

Thr His Val Pro Phe Thr Phe Gly Ser Gly Thr Lys Leu Glu Ile Lys
                100                 105                 110
```

<210> SEQ ID NO 4
<211> LENGTH: 336
<212> TYPE: DNA
<213> ORGANISM: Mus musculus

<400> SEQUENCE: 4

```
gatgttgtga tgacccaaaa cccactctcc ctgcctgtca gtcttggaga tcaagcctcc    60
atctcttgca gatctagtca gagccttata tacaataatg aaacacccta tttacattgg   120
taccggcaga agccaggcca gtctccaaag ctcctgatct acaaagtttc caaccgattt   180
tctggggtcc cagacaggtt cagtggcagt ggatcaggga cagatttcac actcaagatc   240
agcagagtgg aggctgagga tctgggagtt tatttctgct ctcaaagtac acatgttcca   300
ttcacgttcg gctcggggac aaagttggaa ataaaa                             336
```

<210> SEQ ID NO 5
<211> LENGTH: 336
<212> TYPE: DNA
<213> ORGANISM: Mus musculus

<400> SEQUENCE: 5

```
gatgtcgtga tgactcagaa tccactgtcc ctgcctgtgt ccctgggcga tcaggcttcc    60
attagctgtc gttcctctca gtccctgatc tacaacaatg gtaacaccta cctgcactgg   120
tatagacaga agcccggcca gtcccctaag ctgctgatct acaaagtgag taataggttc   180
tcaggagtcc cagaccggtt ttccggcagc ggatctggga ccgatttcac actgaaaatc   240
tctagggtgg aggccgaaga cctgggcgtc tacttttgta gtcagagcac tcacgtcccc   300
ttcaccttcg gcagcggaac aaaactggaa atcaag                             336
```

<210> SEQ ID NO 6
<211> LENGTH: 114
<212> TYPE: PRT
<213> ORGANISM: Mus musculus

<400> SEQUENCE: 6

```
Glu Val Gln Leu Val Glu Ser Gly Gly Gly Leu Val Lys Pro Gly Gly
 1               5                  10                  15

Ser Leu Lys Leu Ser Cys Ala Ala Ser Gly Phe Thr Phe Ser Asp Tyr
                 20                  25                  30

Gly Met Leu Trp Val Arg Gln Ala Pro Glu Lys Gly Leu Glu Trp Ile
            35                  40                  45

Ala Tyr Ile Ser Ser Gly Ser Ser Thr Ile Tyr Tyr Ala Asp Arg Val
 50                  55                  60

Lys Gly Arg Phe Thr Ile Ser Arg Asp Asn Ala Lys Asn Thr Leu Phe
 65              70                  75                  80

Leu Gln Met Thr Ser Leu Arg Ser Glu Asp Thr Ala Met Tyr Tyr Cys
```

```
                     85                  90                  95
Ser Thr Gly Thr Phe Ala Tyr Trp Gly Gln Gly Thr Pro Val Thr Val
            100                 105                 110

Ser Ser

<210> SEQ ID NO 7
<211> LENGTH: 342
<212> TYPE: DNA
<213> ORGANISM: Mus musculus

<400> SEQUENCE: 7
gaggtgcagc tggtggagtc tgggggaggc ttagtgaagc ctggagggtc cctgaaactc      60
tcctgtgcag cctctggatt cactttcagt gactatggaa tgctctgggt tcgtcaggct     120
ccagagaagg ggctggagtg gattgcatac attagtagtg cagtagtac catctactat      180 gcagacagag tgaagggccg attcaccatc tccagagata tgccaagaa caccctgttc      240 ctgcaaatga ccagtctgag atctgaggac acggccatgt attactgttc aactgggacg    300
tttgcttact ggggccaagg gactccggtc actgtcagct ca                        342

<210> SEQ ID NO 8
<211> LENGTH: 342
<212> TYPE: DNA
<213> ORGANISM: Mus musculus

<400> SEQUENCE: 8
gaggtgcagc tggtggagtc tggtggtggt ctggtcaagc ctggaggttc cctgaaactg      60
agttgtgccg catctgggtt tacattctct gactacggaa tgctgtgggt gaggcaggca     120
ccagagaagg gcctggaatg gatcgcttat atttccagcg gatctagtac tatctactat     180
gcagacaggg tcaagggccg gttcaccatt agcagagata cgccaaaaa taccctgttt      240 ctgcagatga catcactgag gtccgaggat accgctatgt attattgctc cacagggact    300
tttgcttact ggggacaggg gacacccgtg accgtcagct ca                        342

<210> SEQ ID NO 9
<211> LENGTH: 112
<212> TYPE: PRT
<213> ORGANISM: Mus musculus

<400> SEQUENCE: 9

Asp Ile Val Met Thr Gln Ala Ala Pro Ser Val Pro Val Thr Pro Gly
1               5                   10                  15

Glu Ser Val Ser Ile Ser Cys Arg Ser Asn Lys Ser Leu Leu His Arg
            20                  25                  30

Asn Gly Asn Thr Tyr Leu Tyr Trp Phe Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Phe Pro Phe Thr Phe Gly Gly Gly Thr Lys Leu Glu Ile Lys
            100                 105                 110

<210> SEQ ID NO 10
<211> LENGTH: 335
```

```
<212> TYPE: DNA
<213> ORGANISM: Mus musculus

<400> SEQUENCE: 10
atattgtgat gactcaggct gcaccctctg tacctgtcac tcctggagag tcagtatcca      60
tctcctgcag gtctaataag agtctcctgc atcgtaatgg caacacttac ttgtattggt     120
ttctgcagag gccaggccag tctcctcagc tcctgatata tcggatgtcc aatcttgcct     180
caggagtccc agacagattc agtggcagtg ggtcaggaac tgctttcaca ctgagaatca     240
gtagagtgga ggctgaggat gtgggtgttt attactgtat gcaacatctg gaatttcctt     300
tcacgttcgg cgggggggacc aagctggaaa taaaa                                335

<210> SEQ ID NO 11
<211> LENGTH: 123
<212> TYPE: PRT
<213> ORGANISM: Mus musculus

<400> SEQUENCE: 11

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Tyr
            20                  25                  30

Tyr Met Asn Trp Val Lys Gln Ser His Gly Lys Ser Leu Glu Trp Ile
        35                  40                  45

Gly Asp Ile Asn Pro Asn Asn Gly Asp Thr Ser Tyr Asn Gln Lys Phe
    50                  55                  60

Lys Gly Lys Ala Pro Leu Thr Val Asp Lys Ser Ser Thr Ala Tyr
65                  70                  75                  80

Met Glu Val Arg Ser Leu Thr Ser Glu Asp Ser Ala Val Tyr Phe Cys
                85                  90                  95

Ala Arg Gly Gly Val Leu Arg Tyr Pro Tyr Tyr Tyr Val Met Asp Tyr
            100                 105                 110

Trp Gly Gln Gly Thr Ser Val Thr Val Ser Ser
        115                 120

<210> SEQ ID NO 12
<211> LENGTH: 369
<212> TYPE: DNA
<213> ORGANISM: Mus musculus

<400> SEQUENCE: 12
gaggtccagc tgcaacaatc tggacctgag ctggtgaagc ctggggcttc agtgaagata      60
tcctgtaagg cttctggata cacgttcact gactactaca tgaactgggt gaagcagagc     120
catggaaaga gccttgagtg gattggagac attaatccta acaatggtga ctactagctac    180 aaccagaaat tcaagggcaa ggccccttg actgtagaca agtcctccag cacagcctac      240
atggaggtcc gcagcctgac atctgaggac tctgcagtct attttctgtgc aagaggagga     300 gtactacggt accgtatta ctatgttatg gactactggg gtcaaggaac ctcagtcact      360
gtcagctca                                                              369

<210> SEQ ID NO 13
<211> LENGTH: 107
<212> TYPE: PRT
<213> ORGANISM: Mus musculus

<400> SEQUENCE: 13
```

Asp Ile Val Met Thr Gln Ser Gln Lys Phe Met Ser Arg Ser Val Gly
1               5                   10                  15

Asp Arg Val Ser Val Thr Cys Lys Ala Ser Gln Asn Val Gly Pro Asn
            20                  25                  30

Val Ala Trp Tyr Gln Gln Arg Pro Gly Gln Ser Pro Lys Pro Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Asn Tyr Pro Tyr
            85                  90                  95

Thr Phe Gly Gly Gly Thr Lys Leu Glu Ile Lys
            100                 105

<210> SEQ ID NO 14
<211> LENGTH: 321
<212> TYPE: DNA
<213> ORGANISM: Mus musculus

<400> SEQUENCE: 14
gacattgtga tgacccagtc tcaaaaattc atgtccagat cagtaggaga cagggtcagc      60
gtcacctgca aggccagtca gaatgtgggt cctaatgtag cctggtatca acagagacca     120
gggcaatctc ctaaaccact gatttactcg gcatcctacc ggtacagtgg agtccctgat     180
cgcttcacag gcagtggatc tgggacagat tcactctca ccatcagcaa tgtgcagtct      240
gaagacttgg cagagtattt ctgtcagcaa tataacaact atccgtacac gttcggaggg     300
gggaccaagc tggaaataaa a                                               321

<210> SEQ ID NO 15
<211> LENGTH: 124
<212> TYPE: PRT
<213> ORGANISM: Mus musculus

<400> SEQUENCE: 15

Glu Val Gln Leu Gln Gln Ser Gly Ala Glu Leu Val Arg Pro Gly Ala
1               5                   10                  15

Ser Val Lys Leu Ser Cys Thr Ala Ser Gly Phe Asn Ile Lys Asp Asp
            20                  25                  30

Tyr Met His Trp Val Lys Gln Arg Pro Glu Gln Gly Leu Glu Trp Ile
        35                  40                  45

Gly Trp Ile Asp Pro Glu Asn Gly His Thr Lys Tyr Ala Ser Lys Phe
    50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
            85                  90                  95

Thr Ser Leu Arg His Tyr Tyr Gly Ser Ser Tyr Val Ser Pro His Tyr
            100                 105                 110

Tyr Trp Gly Gln Gly Thr Thr Leu Thr Val Ser Ser
        115                 120

<210> SEQ ID NO 16
<211> LENGTH: 372
<212> TYPE: DNA
<213> ORGANISM: Mus musculus -continued

<400> SEQUENCE: 16

```
gaggttcagc tgcagcagtc tggggctgag cttgtgaggc caggggcctc agtcaagttg      60
tcctgcacag cttctggctt taatattaaa gacgactata tgcactgggt gaagcagagg     120
cctgaacagg gcctggagtg gattggatgg attgatcctg agaatggtca tactaaatat     180
gcctcgaagt tccagggcaa ggccactata acagcagaca catcctccaa cacagcctac     240
ctgcagctca gcagcctgac atctgaggac actgccgtct attactgtac ttccctccgg     300
cattactacg gtagtagcta cgtatcgccc cattactact ggggccaagg caccactctc     360
actgtcagct ca                                                        372
```

<210> SEQ ID NO 17
<211> LENGTH: 112
<212> TYPE: PRT
<213> ORGANISM: Mus musculus
<220> FEATURE:
<221> NAME/KEY: MISC_FEATURE
<222> LOCATION: (26)..(26)
<223> OTHER INFORMATION: Xaa can be any naturally occurring amino acid
<220> FEATURE:
<221> NAME/KEY: MISC_FEATURE
<222> LOCATION: (28)..(28)
<223> OTHER INFORMATION: Xaa can be any naturally occurring amino acid
<220> FEATURE:
<221> NAME/KEY: MISC_FEATURE
<222> LOCATION: (33)..(34)
<223> OTHER INFORMATION: Xaa can be any naturally occurring amino acid

<400> SEQUENCE: 17

```
Asp Ile Val Met Thr Gln Ala Ala Pro Ser Val Pro Val Thr Pro Gly
1               5                   10                  15

Glu Ser Val Ser Ile Ser Cys Arg Ser Xaa Lys Xaa Leu Leu His Arg
                20                  25                  30

Xaa Xaa Asn Thr Tyr Leu Tyr Trp Phe Leu Gln Arg Pro Gly Gln Ser
            35                  40                  45

Pro Gln Leu Leu Ile Tyr Arg Met Ser Asn Leu Ala Ser Gly Val Pro
        50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Phe Pro Phe Thr Phe Gly Gly Gly Thr Lys Leu Glu Ile Lys
            100                 105                 110
```

<210> SEQ ID NO 18
<211> LENGTH: 123
<212> TYPE: PRT
<213> ORGANISM: Mus musculus
<220> FEATURE:
<221> NAME/KEY: MISC_FEATURE
<222> LOCATION: (55)..(56)
<223> OTHER INFORMATION: Xaa can be any naturally occurring amino acid

<400> SEQUENCE: 18

```
Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Tyr
                20                  25                  30

Tyr Met Asn Trp Val Lys Gln Ser His Gly Lys Ser Leu Glu Trp Ile
            35                  40                  45

Gly Asp Ile Asn Pro Asn Xaa Xaa Asp Thr Ser Tyr Asn Gln Lys Phe
```

```
                    50                  55                  60
Lys Gly Lys Ala Pro Leu Thr Val Asp Lys Ser Ser Ser Thr Ala Tyr
 65                  70                  75                  80

Met Glu Val Arg Ser Leu Thr Ser Glu Asp Ser Ala Val Tyr Phe Cys
                     85                  90                  95

Ala Arg Gly Gly Val Leu Arg Tyr Pro Tyr Tyr Val Met Asp Tyr
                100                 105                 110

Trp Gly Gln Gly Thr Ser Val Thr Val Ser Ser
            115                 120

<210> SEQ ID NO 19
<211> LENGTH: 124
<212> TYPE: PRT
<213> ORGANISM: Mus musculus
<220> FEATURE:
<221> NAME/KEY: MISC_FEATURE
<222> LOCATION: (52)..(53)
<223> OTHER INFORMATION: Xaa can be any naturally occurring amino acid
<220> FEATURE:
<221> NAME/KEY: MISC_FEATURE
<222> LOCATION: (55)..(56)
<223> OTHER INFORMATION: Xaa can be any naturally occurring amino acid

<400> SEQUENCE: 19

Glu Val Gln Leu Gln Gln Ser Gly Ala Glu Leu Val Arg Pro Gly Ala
 1               5                  10                  15

Ser Val Lys Leu Ser Cys Thr Ala Ser Gly Phe Asn Ile Lys Asp Asp
                20                  25                  30

Tyr Met His Trp Val Lys Gln Arg Pro Glu Gln Gly Leu Glu Trp Ile
            35                  40                  45

Gly Trp Ile Xaa Xaa Glu Xaa Xaa His Thr Lys Tyr Ala Ser Lys Phe
        50                  55                  60

Gln Gly Lys Ala Thr Ile Thr Ala Asp Thr Ser Ser Asn Thr Ala Tyr
 65                  70                  75                  80

Leu Gln Leu Ser Ser Leu Thr Ser Glu Asp Thr Ala Val Tyr Tyr Cys
                 85                  90                  95

Thr Ser Leu Arg His Tyr Tyr Gly Ser Ser Tyr Val Ser Pro His Tyr
                100                 105                 110

Tyr Trp Gly Gln Gly Thr Thr Leu Thr Val Ser Ser
            115                 120

<210> SEQ ID NO 20
<211> LENGTH: 5
<212> TYPE: PRT
<213> ORGANISM: Mus musculus

<400> SEQUENCE: 20

Asp Tyr Gly Met Leu
 1               5

<210> SEQ ID NO 21
<211> LENGTH: 7
<212> TYPE: PRT
<213> ORGANISM: Mus musculus

<400> SEQUENCE: 21

Gly Phe Thr Phe Ser Asp Tyr
 1               5

<210> SEQ ID NO 22
<211> LENGTH: 17
```

```
<212> TYPE: PRT
<213> ORGANISM: Mus musculus

<400> SEQUENCE: 22

Tyr Ile Ser Ser Gly Ser Ser Thr Ile Tyr Tyr Ala Asp Arg Val Lys
1               5                   10                  15

Gly

<210> SEQ ID NO 23
<211> LENGTH: 6
<212> TYPE: PRT
<213> ORGANISM: Mus musculus

<400> SEQUENCE: 23

Ser Ser Gly Ser Ser Thr
1               5

<210> SEQ ID NO 24
<211> LENGTH: 5
<212> TYPE: PRT
<213> ORGANISM: Mus musculus

<400> SEQUENCE: 24

Gly Thr Phe Ala Tyr
1               5

<210> SEQ ID NO 25
<211> LENGTH: 16
<212> TYPE: PRT
<213> ORGANISM: Mus musculus

<400> SEQUENCE: 25

Arg Ser Ser Gln Ser Leu Ile Tyr Asn Asn Gly Asn Thr Tyr Leu His
1               5                   10                  15

<210> SEQ ID NO 26
<211> LENGTH: 12
<212> TYPE: PRT
<213> ORGANISM: Mus musculus

<400> SEQUENCE: 26

Ser Gln Ser Leu Ile Tyr Asn Asn Gly Asn Thr Tyr
1               5                   10

<210> SEQ ID NO 27
<211> LENGTH: 7
<212> TYPE: PRT
<213> ORGANISM: Mus musculus

<400> SEQUENCE: 27

Lys Val Ser Asn Arg Phe Ser
1               5

<210> SEQ ID NO 28

<400> SEQUENCE: 28

000

<210> SEQ ID NO 29
<211> LENGTH: 9
<212> TYPE: PRT
<213> ORGANISM: Mus musculus

<400> SEQUENCE: 29
```

Ser Gln Ser Thr His Val Pro Phe Thr
1               5

<210> SEQ ID NO 30
<211> LENGTH: 6
<212> TYPE: PRT
<213> ORGANISM: Mus musculus

<400> SEQUENCE: 30

Ser Thr His Val Pro Phe
1               5

<210> SEQ ID NO 31
<211> LENGTH: 5
<212> TYPE: PRT
<213> ORGANISM: Mus musculus

<400> SEQUENCE: 31

Asp Asp Tyr Met His
1               5

<210> SEQ ID NO 32
<211> LENGTH: 7
<212> TYPE: PRT
<213> ORGANISM: Mus musculus

<400> SEQUENCE: 32

Gly Phe Asn Ile Lys Asp Asp
1               5

<210> SEQ ID NO 33
<211> LENGTH: 17
<212> TYPE: PRT
<213> ORGANISM: Mus musculus

<400> SEQUENCE: 33

Trp Ile Asp Pro Glu Asn Gly His Thr Lys Tyr Ala Ser Lys Phe Gln
1               5                   10                  15

Gly

<210> SEQ ID NO 34
<211> LENGTH: 6
<212> TYPE: PRT
<213> ORGANISM: Mus musculus

<400> SEQUENCE: 34

Asp Pro Glu Asn Gly His
1               5

<210> SEQ ID NO 35
<211> LENGTH: 15
<212> TYPE: PRT
<213> ORGANISM: Mus musculus

<400> SEQUENCE: 35

Leu Arg His Tyr Tyr Gly Ser Ser Tyr Val Ser Pro His Tyr Tyr
1               5                   10                  15

<210> SEQ ID NO 36
<211> LENGTH: 15
<212> TYPE: PRT
<213> ORGANISM: Mus musculus

<400> SEQUENCE: 36

Leu Arg His Tyr Tyr Gly Ser Ser Tyr Val Ser Pro His Tyr Tyr
1               5                   10                  15

<210> SEQ ID NO 37
<211> LENGTH: 11
<212> TYPE: PRT
<213> ORGANISM: Mus musculus

<400> SEQUENCE: 37

Lys Ala Ser Gln Asn Val Gly Pro Asn Val Ala
1               5                   10

<210> SEQ ID NO 38
<211> LENGTH: 7
<212> TYPE: PRT
<213> ORGANISM: Mus musculus

<400> SEQUENCE: 38

Ser Gln Asn Val Gly Pro Asn
1               5

<210> SEQ ID NO 39
<211> LENGTH: 7
<212> TYPE: PRT
<213> ORGANISM: Mus musculus

<400> SEQUENCE: 39

Ser Ala Ser Tyr Arg Tyr Ser
1               5

<210> SEQ ID NO 40

<400> SEQUENCE: 40

000

<210> SEQ ID NO 41
<211> LENGTH: 9
<212> TYPE: PRT
<213> ORGANISM: Mus musculus

<400> SEQUENCE: 41

Gln Gln Tyr Asn Asn Tyr Pro Tyr Thr
1               5

<210> SEQ ID NO 42
<211> LENGTH: 6
<212> TYPE: PRT
<213> ORGANISM: Mus musculus

<400> SEQUENCE: 42

Tyr Asn Asn Tyr Pro Tyr
1               5

<210> SEQ ID NO 43
<211> LENGTH: 5
<212> TYPE: PRT
<213> ORGANISM: Mus musculus

<400> SEQUENCE: 43

Asp Tyr Tyr Met Asn
1               5

<210> SEQ ID NO 44

```
<211> LENGTH: 7
<212> TYPE: PRT
<213> ORGANISM: Mus musculus

<400> SEQUENCE: 44

Gly Tyr Thr Phe Thr Asp Tyr
1               5

<210> SEQ ID NO 45
<211> LENGTH: 17
<212> TYPE: PRT
<213> ORGANISM: Mus musculus

<400> SEQUENCE: 45

Asp Ile Asn Pro Asn Asn Gly Asp Thr Ser Tyr Asn Gln Lys Phe Lys
1               5                   10                  15

Gly

<210> SEQ ID NO 46
<211> LENGTH: 6
<212> TYPE: PRT
<213> ORGANISM: Mus musculus

<400> SEQUENCE: 46

Asn Pro Asn Asn Gly Asp
1               5

<210> SEQ ID NO 47
<211> LENGTH: 14
<212> TYPE: PRT
<213> ORGANISM: Mus musculus

<400> SEQUENCE: 47

Gly Gly Val Leu Arg Tyr Pro Tyr Tyr Tyr Val Met Asp Tyr
1               5                   10

<210> SEQ ID NO 48
<211> LENGTH: 14
<212> TYPE: PRT
<213> ORGANISM: Mus musculus

<400> SEQUENCE: 48

Gly Gly Val Leu Arg Tyr Pro Tyr Tyr Tyr Val Met Asp Tyr
1               5                   10

<210> SEQ ID NO 49
<211> LENGTH: 16
<212> TYPE: PRT
<213> ORGANISM: Mus musculus

<400> SEQUENCE: 49

Arg Ser Asn Lys Ser Leu Leu His Arg Asn Gly Asn Thr Tyr Leu Tyr
1               5                   10                  15

<210> SEQ ID NO 50
<211> LENGTH: 12
<212> TYPE: PRT
<213> ORGANISM: Mus musculus

<400> SEQUENCE: 50

Asn Lys Ser Leu Leu His Arg Asn Gly Asn Thr Tyr
1               5                   10

<210> SEQ ID NO 51
```

-continued

```
<211> LENGTH: 7
<212> TYPE: PRT
<213> ORGANISM: Mus musculus

<400> SEQUENCE: 51

Arg Met Ser Asn Leu Ala Ser
1               5

<210> SEQ ID NO 52

<400> SEQUENCE: 52

000

<210> SEQ ID NO 53
<211> LENGTH: 9
<212> TYPE: PRT
<213> ORGANISM: Mus musculus

<400> SEQUENCE: 53

Met Gln His Leu Glu Phe Pro Phe Thr
1               5

<210> SEQ ID NO 54
<211> LENGTH: 6
<212> TYPE: PRT
<213> ORGANISM: Mus musculus

<400> SEQUENCE: 54

His Leu Glu Phe Pro Phe
1               5

<210> SEQ ID NO 55
<211> LENGTH: 110
<212> TYPE: PRT
<213> ORGANISM: Canis familiaris

<400> SEQUENCE: 55

Arg Asn Asp Ala Gln Pro Ala Val Tyr Leu Phe Gln Pro Ser Pro Asp
1               5                   10                  15

Gln Leu His Thr Gly Ser Ala Ser Val Val Cys Leu Leu Asn Ser Phe
            20                  25                  30

Tyr Pro Lys Asp Ile Asn Val Lys Trp Lys Val Asp Gly Val Ile Gln
        35                  40                  45

Asp Thr Gly Ile Gln Glu Ser Val Thr Glu Gln Asp Lys Asp Ser Thr
    50                  55                  60

Tyr Ser Leu Ser Ser Thr Leu Thr Met Ser Ser Thr Glu Tyr Leu Ser
65                  70                  75                  80

His Glu Leu Tyr Ser Cys Glu Ile Thr His Lys Ser Leu Pro Ser Thr
                85                  90                  95

Leu Ile Lys Ser Phe Gln Arg Ser Glu Cys Gln Arg Val Asp
            100                 105                 110

<210> SEQ ID NO 56
<211> LENGTH: 330
<212> TYPE: DNA
<213> ORGANISM: Canis familiaris

<400> SEQUENCE: 56
cgtaacgacg cccagcctgc cgtgtatctg ttccagccct cccccgatca gctgcatacc     60
gggtccgcct cagtggtgtg cctgctgaac agtttctacc ccaaggacat caatgtgaag    120
```

```
tggaaagtgg acggcgtcat ccaggatact ggcatccagg agagcgtcac cgaacaggac    180
aaagattcaa catattccct gtccagcacc ctgacaatgt ctagtactga gtacctgagc    240
cacgaactgt attcttgcga gattacccat aagagcctgc catccaccct gattaagagt    300
ttccagcgtt ccgaatgcca gagagtcgat                                    330
```

<210> SEQ ID NO 57
<211> LENGTH: 335
<212> TYPE: PRT
<213> ORGANISM: Canis familiaris

<400> SEQUENCE: 57

```
Ala Ser Thr Thr Ala Pro Ser Val Phe Pro Leu Ala Pro Ser Cys Gly
1               5                   10                  15

Ser Thr Ser Gly Ser Thr Val Ala Leu Ala Cys Leu Val Ser Gly Tyr
            20                  25                  30

Phe Pro Glu Pro Val Thr Val Ser Trp Asn Ser Gly Ser Leu Thr Ser
        35                  40                  45

Gly Val His Thr Phe Pro Ser Val Leu Gln Ser Ser Gly Leu Tyr Ser
    50                  55                  60

Leu Ser Ser Met Val Thr Val Pro Ser Ser Arg Trp Pro Ser Glu Thr
65                  70                  75                  80

Phe Thr Cys Asn Val Ala His Pro Ala Ser Lys Thr Lys Val Asp Lys
                85                  90                  95

Pro Val Pro Lys Arg Glu Asn Gly Arg Val Pro Arg Pro Pro Asp Cys
            100                 105                 110

Pro Lys Cys Pro Ala Pro Glu Met Leu Gly Gly Pro Ser Val Phe Ile
        115                 120                 125

Phe Pro Pro Lys Pro Lys Asp Thr Leu Leu Ile Ala Arg Thr Pro Glu
    130                 135                 140

Val Thr Cys Val Val Val Asp Leu Asp Pro Glu Asp Pro Glu Val Gln
145                 150                 155                 160

Ile Ser Trp Phe Val Asp Gly Lys Gln Met Gln Thr Ala Lys Thr Gln
                165                 170                 175

Pro Arg Glu Glu Gln Phe Asn Gly Thr Tyr Arg Val Val Ser Val Leu
            180                 185                 190

Pro Ile Gly His Gln Asp Trp Leu Lys Gly Lys Gln Phe Thr Cys Lys
        195                 200                 205

Val Asn Asn Lys Ala Leu Pro Ser Pro Ile Glu Arg Thr Ile Ser Lys
    210                 215                 220

Ala Arg Gly Gln Ala His Gln Pro Ser Val Tyr Val Leu Pro Pro Ser
225                 230                 235                 240

Arg Glu Glu Leu Ser Lys Asn Thr Val Ser Leu Thr Cys Leu Ile Lys
                245                 250                 255

Asp Phe Phe Pro Pro Asp Ile Asp Val Glu Trp Gln Ser Asn Gly Gln
            260                 265                 270

Gln Glu Pro Glu Ser Lys Tyr Arg Thr Thr Pro Pro Gln Leu Asp Glu
        275                 280                 285

Asp Gly Ser Tyr Phe Leu Tyr Ser Lys Leu Ser Val Asp Lys Ser Arg
    290                 295                 300

Trp Gln Arg Gly Asp Thr Phe Ile Cys Ala Val Met His Glu Ala Leu
305                 310                 315                 320

His Asn His Tyr Thr Gln Lys Ser Leu Ser His Ser Pro Gly Lys
                325                 330                 335
```

<210> SEQ ID NO 58
<211> LENGTH: 1005
<212> TYPE: DNA
<213> ORGANISM: Canis familiaris

<400> SEQUENCE: 58

| | | | | | |
|---|---|---|---|---|---|
| gcgtcaacta | ccgctccctc | cgtcttccct | ctggctcctt | catgtggttc | aacaagtggc | 60 |
| agtaccgtcg | ccctggcttg | cctggtgtca | gggtacttcc | ctgagccagt | caccgtgtcc | 120 |
| tggaacagcg | ggtctctgac | aagtggtgtc | cacactttc | cttcagtgct | gcagtccagc | 180 |
| ggtctgtatt | ccctgtctag | tatggtcact | gtgccatcat | ccagatggcc | cagcgaaact | 240 |
| ttcacctgta | acgtggcaca | tccagcctct | aagaccaaag | tggacaagcc | cgtgcctaaa | 300 |
| cgagagaatg | gaagggtgcc | tcgaccacct | gattgcccaa | agtgtccagc | accagaaatg | 360 |
| ctgggaggac | catccgtgtt | catctttcca | cccaagccta | agacacact | gctgattgct | 420 |
| aggaccccag | aggtgacatg | cgtggtcgtg | gacctggatc | ccgaggaccc | tgaagtccag | 480 |
| atcagctggt | tcgtggatgg | gaagcagatg | cagacagcaa | aaactcagcc | aagggaggaa | 540 |
| cagtttaatg | gtacttaccg | ggtcgtgtct | gtgctgccca | ttggccacca | ggactggctg | 600 |
| aagggaaaac | agtttacctg | caaggtgaac | aacaaggctc | tgccttcccc | aatcgagcga | 660 |
| acaattagca | aggctcgtgg | ccaggcacat | cagcccagcg | tctacgtgct | gcctccatcc | 720 |
| cgagaggaac | tgagcaagaa | cactgtgtct | ctgacctgtc | tgatcaaaga | tttctttccc | 780 |
| cctgacattg | atgtggagtg | gcagtctaat | ggacagcagg | agcctgagag | taagtatcgg | 840 |
| accacaccac | cccagctgga | cgaagatggc | agttacttcc | tgtatagtaa | gctgtcagtg | 900 |
| gacaaatcca | gatggcagcg | cggagatacc | ttcatctgtg | ccgtgatgca | cgaagcactg | 960 |
| cacaatcact | acacacagaa | gtcactgagc | cactctccag | ggaaa | | 1005 |

<210> SEQ ID NO 59
<211> LENGTH: 47
<212> TYPE: PRT
<213> ORGANISM: Canis familiaris

<400> SEQUENCE: 59

Asn Ile Thr Ile Ser His Phe Phe Lys Met Glu Asn Leu Asn Leu Ile
1               5                   10                  15

Lys Ala Pro Met Pro Tyr Val Asp Ile His Asn Cys Asp Pro Ala Asn
            20                  25                  30

Pro Ser Glu Lys Asn Ser Leu Ser Ile Gln Tyr Cys Gly Ser Ile
        35                  40                  45

<210> SEQ ID NO 60
<211> LENGTH: 239
<212> TYPE: PRT
<213> ORGANISM: Canis familiaris

<400> SEQUENCE: 60

Arg Ser Leu Glu Val Leu Phe Gln Gly Pro Gly Ser Pro Pro Leu Lys
1               5                   10                  15

Glu Cys Pro Pro Cys Ala Ala Pro Asp Leu Leu Gly Gly Pro Ser Val
            20                  25                  30

Phe Ile Phe Pro Pro Lys Ile Lys Asp Val Leu Met Ile Ser Leu Ser
        35                  40                  45

Pro Met Val Thr Cys Val Val Val Asp Val Ser Glu Asp Asp Pro Asp
    50                  55                  60

Val Gln Ile Ser Trp Phe Val Asn Asn Val Glu Val His Thr Ala Gln
65                  70                  75                  80

Thr Gln Thr His Arg Glu Asp Tyr Asn Ser Thr Leu Arg Val Val Ser
                85                  90                  95

Ala Leu Pro Ile Gln His Gln Asp Trp Met Ser Gly Lys Glu Phe Lys
            100                 105                 110

Cys Lys Val Asn Asn Arg Ala Leu Pro Ser Pro Ile Glu Lys Thr Ile
        115                 120                 125

Ser Lys Pro Arg Gly Pro Val Arg Ala Pro Gln Val Tyr Val Leu Pro
    130                 135                 140

Pro Pro Ala Glu Glu Met Thr Lys Lys Glu Phe Ser Leu Thr Cys Met
145                 150                 155                 160

Ile Thr Gly Phe Leu Pro Ala Glu Ile Ala Val Asp Trp Thr Ser Asn
                165                 170                 175

Gly Arg Thr Glu Gln Asn Tyr Lys Asn Thr Ala Thr Val Leu Asp Ser
            180                 185                 190

Asp Gly Ser Tyr Phe Met Tyr Ser Lys Leu Arg Val Gln Lys Ser Thr
        195                 200                 205

Trp Glu Arg Gly Ser Leu Phe Ala Cys Ser Val His Glu Gly Leu
210                 215                 220

His Asn His Leu Thr Thr Lys Thr Ile Ser Arg Ser Leu Gly Lys
225                 230                 235

<210> SEQ ID NO 61
<211> LENGTH: 286
<212> TYPE: PRT
<213> ORGANISM: Canis familiaris

<400> SEQUENCE: 61

Asn Ile Thr Ile Ser His Phe Phe Lys Met Glu Asn Leu Asn Leu Ile
1               5                   10                  15

Lys Ala Pro Met Pro Tyr Val Asp Ile His Asn Cys Asp Pro Ala Asn
            20                  25                  30

Pro Ser Glu Lys Asn Ser Leu Ser Ile Gln Tyr Cys Gly Ser Ile Arg
        35                  40                  45

Ser Leu Glu Val Leu Phe Gln Gly Pro Gly Ser Pro Pro Leu Lys Glu
50                  55                  60

Cys Pro Pro Cys Ala Ala Pro Asp Leu Leu Gly Gly Pro Ser Val Phe
65                  70                  75                  80

Ile Phe Pro Pro Lys Ile Lys Asp Val Leu Met Ile Ser Leu Ser Pro
                85                  90                  95

Met Val Thr Cys Val Val Val Asp Val Ser Glu Asp Asp Pro Asp Val
            100                 105                 110

Gln Ile Ser Trp Phe Val Asn Asn Val Glu Val His Thr Ala Gln Thr
        115                 120                 125

Gln Thr His Arg Glu Asp Tyr Asn Ser Thr Leu Arg Val Val Ser Ala
    130                 135                 140

Leu Pro Ile Gln His Gln Asp Trp Met Ser Gly Lys Glu Phe Lys Cys
145                 150                 155                 160

Lys Val Asn Asn Arg Ala Leu Pro Ser Pro Ile Glu Lys Thr Ile Ser
                165                 170                 175

Lys Pro Arg Gly Pro Val Arg Ala Pro Gln Val Tyr Val Leu Pro Pro
            180                 185                 190

Pro Ala Glu Glu Met Thr Lys Lys Glu Phe Ser Leu Thr Cys Met Ile
        195                 200                 205

```
Thr Gly Phe Leu Pro Ala Glu Ile Ala Val Asp Trp Thr Ser Asn Gly
    210                 215                 220

Arg Thr Glu Gln Asn Tyr Lys Asn Thr Ala Thr Val Leu Asp Ser Asp
225                 230                 235                 240

Gly Ser Tyr Phe Met Tyr Ser Lys Leu Arg Val Gln Lys Ser Thr Trp
                245                 250                 255

Glu Arg Gly Ser Leu Phe Ala Cys Ser Val Val His Glu Gly Leu His
            260                 265                 270

Asn His Leu Thr Thr Lys Thr Ile Ser Arg Ser Leu Gly Lys
        275                 280                 285

<210> SEQ ID NO 62
<211> LENGTH: 47
<212> TYPE: PRT
<213> ORGANISM: Canis familiaris

<400> SEQUENCE: 62

Asn Ile Thr Ile Ser His Phe Phe Lys Met Glu Asn Leu Asn Leu Ile
1               5                   10                  15

Lys Ala Pro Met Pro Tyr Val Asp Ile His Asn Cys Asp Pro Ala Asn
            20                  25                  30

Pro Ser Glu Lys Asn Ser Leu Ser Ile Gln Tyr Cys Gly Ser Ile
        35                  40                  45

<210> SEQ ID NO 63
<211> LENGTH: 47
<212> TYPE: PRT
<213> ORGANISM: Artificial Sequence
<220> FEATURE:
<223> OTHER INFORMATION: Hybrid human-canine CD20 peptide

<400> SEQUENCE: 63

Asn Ile Thr Ile Ser His Phe Phe Lys Met Glu Asn Leu Asn Phe Ile
1               5                   10                  15

Arg Ala His Thr Pro Tyr Ile Asn Ile Tyr Asn Cys Glu Pro Ala Asn
            20                  25                  30

Pro Ser Glu Lys Asn Ser Pro Ser Thr Gln Tyr Cys Tyr Ser Ile
        35                  40                  45

<210> SEQ ID NO 64
<211> LENGTH: 47
<212> TYPE: PRT
<213> ORGANISM: Artificial Sequence
<220> FEATURE:
<223> OTHER INFORMATION: Hybrid human-canine CD20 peptide

<400> SEQUENCE: 64

Asn Ile Thr Ile Ser His Phe Phe Lys Met Glu Asn Leu Asn Leu Ile
1               5                   10                  15

Lys Ala Pro Met Pro Tyr Val Asn Ile Tyr Asn Cys Glu Pro Ala Asn
            20                  25                  30

Pro Ser Glu Lys Asn Ser Pro Ser Thr Gln Tyr Cys Tyr Ser Ile
        35                  40                  45

<210> SEQ ID NO 65
<211> LENGTH: 47
<212> TYPE: PRT
<213> ORGANISM: Artificial Sequence
<220> FEATURE:
<223> OTHER INFORMATION: Hybrid human-canine CD20 peptide
```

-continued

<400> SEQUENCE: 65

Asn Ile Thr Ile Ser His Phe Phe Lys Met Glu Asn Leu Asn Leu Ile
1               5                   10                  15

Lys Ala Pro Met Pro Tyr Val Asp Ile His Asn Cys Asp Pro Ala Asn
            20                  25                  30

Pro Ser Glu Lys Asn Ser Pro Ser Thr Gln Tyr Cys Tyr Ser Ile
        35                  40                  45

<210> SEQ ID NO 66
<211> LENGTH: 47
<212> TYPE: PRT
<213> ORGANISM: Artificial Sequence
<220> FEATURE:
<223> OTHER INFORMATION: Hybrid human-canine CD20 peptide

<400> SEQUENCE: 66

Asn Ile Thr Ile Ser His Phe Phe Lys Met Glu Asn Leu Asn Leu Ile
1               5                   10                  15

Lys Ala Pro Met Pro Tyr Val Asn Ile Tyr Asn Cys Glu Pro Ala Asn
            20                  25                  30

Pro Ser Glu Lys Asn Ser Leu Ser Ile Gln Tyr Cys Gly Ser Ile
        35                  40                  45

<210> SEQ ID NO 67
<211> LENGTH: 47
<212> TYPE: PRT
<213> ORGANISM: Homo sapiens

<400> SEQUENCE: 67

Asn Ile Lys Ile Ser His Phe Leu Lys Met Glu Ser Leu Asn Phe Ile
1               5                   10                  15

Arg Ala His Thr Pro Tyr Ile Asn Ile Tyr Asn Cys Glu Pro Ala Asn
            20                  25                  30

Pro Ser Glu Lys Asn Ser Pro Ser Thr Gln Tyr Cys Tyr Ser Ile
        35                  40                  45

<210> SEQ ID NO 68
<211> LENGTH: 39
<212> TYPE: DNA
<213> ORGANISM: Mus musculus

<400> SEQUENCE: 68
gcgtctagaa yctccacaca caggrrccag tggatagac                              39

<210> SEQ ID NO 69
<211> LENGTH: 29
<212> TYPE: DNA
<213> ORGANISM: Mus musculus

<400> SEQUENCE: 69
gcgtctagaa ctggatggtg ggaagatgg                                         29

<210> SEQ ID NO 70
<211> LENGTH: 16
<212> TYPE: PRT
<213> ORGANISM: Mus musculus

<400> SEQUENCE: 70

Arg Ser Ser Gln Ser Leu Ile Tyr Asn Lys Gly Asn Thr Tyr Leu His
1               5                   10                  15

<210> SEQ ID NO 71
<211> LENGTH: 12
<212> TYPE: PRT
<213> ORGANISM: Mus musculus

<400> SEQUENCE: 71

Ser Gln Ser Leu Ile Tyr Asn Lys Gly Asn Thr Tyr
1               5                   10

<210> SEQ ID NO 72
<211> LENGTH: 16
<212> TYPE: PRT
<213> ORGANISM: Mus musculus

<400> SEQUENCE: 72

Arg Ser Ser Gln Ser Leu Ile Tyr Asn Asn Lys Asn Thr Tyr Leu His
1               5                   10                  15

<210> SEQ ID NO 73
<211> LENGTH: 12
<212> TYPE: PRT
<213> ORGANISM: Mus musculus

<400> SEQUENCE: 73

Ser Gln Ser Leu Ile Tyr Asn Asn Lys Asn Thr Tyr
1               5                   10

<210> SEQ ID NO 74
<211> LENGTH: 16
<212> TYPE: PRT
<213> ORGANISM: Mus musculus

<400> SEQUENCE: 74

Arg Ser Ser Gln Ser Leu Ile Tyr Asn Asn Gln Asn Thr Tyr Leu His
1               5                   10                  15

<210> SEQ ID NO 75
<211> LENGTH: 12
<212> TYPE: PRT
<213> ORGANISM: Mus musculus

<400> SEQUENCE: 75

Ser Gln Ser Leu Ile Tyr Asn Asn Gln Asn Thr Tyr
1               5                   10

<210> SEQ ID NO 76
<211> LENGTH: 16
<212> TYPE: PRT
<213> ORGANISM: Mus musculus

<400> SEQUENCE: 76

Arg Ser Ser Gln Ser Leu Ile Tyr Asn Asn Ala Asn Thr Tyr Leu His
1               5                   10                  15

<210> SEQ ID NO 77
<211> LENGTH: 12
<212> TYPE: PRT
<213> ORGANISM: Mus musculus

<400> SEQUENCE: 77

Ser Gln Ser Leu Ile Tyr Asn Asn Ala Asn Thr Tyr
1               5                   10

<210> SEQ ID NO 78
<211> LENGTH: 110

```
<212> TYPE: PRT
<213> ORGANISM: Canis familiaris

<400> SEQUENCE: 78

Arg Thr Asp Ala Gln Pro Ala Val Tyr Leu Phe Gln Pro Ser Pro Asp
1               5                   10                  15

Gln Leu His Thr Gly Ser Ala Ser Val Val Cys Leu Leu Asn Ser Phe
            20                  25                  30

Tyr Pro Lys Asp Ile Asn Val Lys Trp Lys Val Asp Gly Val Ile Gln
        35                  40                  45

Asp Thr Gly Ile Gln Glu Ser Val Thr Glu Gln Asp Lys Asp Ser Thr
    50                  55                  60

Tyr Ser Leu Ser Ser Thr Leu Thr Met Ser Ser Thr Glu Tyr Leu Ser
65                  70                  75                  80

His Glu Leu Tyr Ser Cys Glu Ile Thr His Lys Ser Leu Pro Ser Thr
                85                  90                  95

Leu Ile Lys Ser Phe Gln Arg Ser Glu Cys Gln Arg Val Asp
            100                 105                 110

<210> SEQ ID NO 79
<211> LENGTH: 110
<212> TYPE: PRT
<213> ORGANISM: Canis familiaris

<400> SEQUENCE: 79

Arg Asn Asp Ala Gln Pro Ala Val Tyr Leu Phe Gln Pro Ser Pro Asp
1               5                   10                  15

Gln Leu His Thr Gly Ser Ala Ser Val Val Cys Leu Leu Ser Ser Phe
            20                  25                  30

Tyr Pro Lys Asp Ile Asn Val Lys Trp Lys Val Asp Gly Val Ile Gln
        35                  40                  45

Asp Thr Gly Ile Gln Glu Ser Val Thr Glu Gln Asp Lys Asp Ser Thr
    50                  55                  60

Tyr Ser Leu Ser Ser Thr Leu Thr Met Ser Ser Thr Glu Tyr Leu Ser
65                  70                  75                  80

His Glu Leu Tyr Ser Cys Glu Ile Thr His Lys Ser Leu Pro Ser Thr
                85                  90                  95

Leu Ile Lys Ser Phe Gln Arg Ser Glu Cys Gln Arg Val Asp
            100                 105                 110

<210> SEQ ID NO 80
<211> LENGTH: 110
<212> TYPE: PRT
<213> ORGANISM: Canis familiaris

<400> SEQUENCE: 80

Arg Thr Asp Ala Gln Pro Ala Val Tyr Leu Phe Gln Pro Ser Pro Asp
1               5                   10                  15

Gln Leu His Thr Gly Ser Ala Ser Val Val Cys Leu Leu Ser Ser Phe
            20                  25                  30

Tyr Pro Lys Asp Ile Asn Val Lys Trp Lys Val Asp Gly Val Ile Gln
        35                  40                  45

Asp Thr Gly Ile Gln Glu Ser Val Thr Glu Gln Asp Lys Asp Ser Thr
    50                  55                  60

Tyr Ser Leu Ser Ser Thr Leu Thr Met Ser Ser Thr Glu Tyr Leu Ser
65                  70                  75                  80

His Glu Leu Tyr Ser Cys Glu Ile Thr His Lys Ser Leu Pro Ser Thr
```

```
            85                  90                  95
Leu Ile Lys Ser Phe Gln Arg Ser Glu Cys Gln Arg Val Asp
            100                 105                 110

<210> SEQ ID NO 81
<211> LENGTH: 335
<212> TYPE: PRT
<213> ORGANISM: Canis familiaris

<400> SEQUENCE: 81

Ala Ser Thr Thr Ala Pro Ser Val Phe Pro Leu Ala Pro Ser Cys Gly
1               5                   10                  15

Ser Thr Ser Gly Ser Thr Val Ala Leu Ala Cys Leu Val Ser Gly Tyr
                20                  25                  30

Phe Pro Glu Pro Val Thr Val Ser Trp Asn Ser Gly Ser Leu Thr Ser
            35                  40                  45

Gly Val His Thr Phe Pro Ser Val Leu Gln Ser Ser Gly Leu Tyr Ser
        50                  55                  60

Leu Ser Ser Met Val Thr Val Pro Ser Ser Arg Trp Pro Ser Glu Thr
65                  70                  75                  80

Phe Thr Cys Asn Val Ala His Pro Ala Ser Lys Thr Lys Val Asp Lys
                85                  90                  95

Pro Val Pro Lys Arg Glu Asn Gly Arg Val Pro Arg Pro Pro Asp Cys
            100                 105                 110

Pro Lys Cys Pro Ala Pro Glu Pro Ala Gly Gly Pro Ser Val Phe Ile
        115                 120                 125

Phe Pro Pro Lys Pro Lys Asp Thr Leu Leu Ile Ala Arg Thr Pro Glu
    130                 135                 140

Val Thr Cys Val Val Val Asp Leu Asp Pro Glu Asp Pro Glu Val Gln
145                 150                 155                 160

Ile Ser Trp Phe Val Asp Gly Lys Gln Met Gln Thr Ala Lys Thr Gln
                165                 170                 175

Pro Arg Glu Glu Gln Phe Asn Gly Thr Tyr Arg Val Val Ser Val Leu
            180                 185                 190

Pro Ile Gly His Gln Asp Trp Leu Lys Gly Lys Gln Phe Thr Cys Lys
        195                 200                 205

Val Asn Asn Lys Ala Leu Pro Ser Pro Ile Glu Arg Thr Ile Ser Lys
    210                 215                 220

Ala Arg Gly Gln Ala His Gln Pro Ser Val Tyr Val Leu Pro Pro Ser
225                 230                 235                 240

Arg Glu Glu Leu Ser Lys Asn Thr Val Ser Leu Thr Cys Leu Ile Lys
                245                 250                 255

Asp Phe Phe Pro Pro Asp Ile Asp Val Glu Trp Gln Ser Asn Gly Gln
            260                 265                 270

Gln Glu Pro Glu Ser Lys Tyr Arg Thr Thr Pro Pro Gln Leu Asp Glu
        275                 280                 285

Asp Gly Ser Tyr Phe Leu Tyr Ser Lys Leu Ser Val Asp Lys Ser Arg
    290                 295                 300

Trp Gln Arg Gly Asp Thr Phe Ile Cys Ala Val Met His Glu Ala Leu
305                 310                 315                 320

His Asn His Tyr Thr Gln Lys Ser Leu Ser His Ser Pro Gly Lys
                325                 330                 335

<210> SEQ ID NO 82
<211> LENGTH: 335
```

<212> TYPE: PRT
<213> ORGANISM: Canis familiaris

<400> SEQUENCE: 82

Ala Ser Thr Thr Ala Pro Ser Val Phe Pro Leu Ala Pro Ser Cys Gly
1               5                   10                  15

Ser Thr Ser Gly Ser Thr Val Ala Leu Ala Cys Leu Val Ser Gly Tyr
                20                  25                  30

Phe Pro Glu Pro Val Thr Val Ser Trp Asn Ser Gly Ser Leu Thr Ser
            35                  40                  45

Gly Val His Thr Phe Pro Ser Val Leu Gln Ser Ser Gly Leu Tyr Ser
        50                  55                  60

Leu Ser Ser Met Val Thr Val Pro Ser Ser Arg Trp Pro Ser Glu Thr
65                  70                  75                  80

Phe Thr Cys Asn Val Ala His Pro Ala Ser Lys Thr Lys Val Asp Lys
                85                  90                  95

Pro Val Pro Lys Arg Glu Asn Gly Arg Val Pro Arg Pro Asp Cys
            100                 105                 110

Pro Lys Cys Pro Ala Pro Glu Met Leu Gly Gly Pro Ser Val Phe Ile
            115                 120                 125

Phe Pro Pro Lys Pro Lys Asp Thr Leu Leu Ile Ala Arg Thr Pro Glu
130                 135                 140

Val Thr Cys Val Val Val Asp Leu Asp Pro Glu Asp Pro Glu Val Gln
145                 150                 155                 160

Ile Ser Trp Phe Val Asp Gly Lys Gln Met Gln Thr Ala Lys Thr Gln
                165                 170                 175

Pro Arg Glu Glu Gln Phe Ala Gly Thr Tyr Arg Val Val Ser Val Leu
            180                 185                 190

Pro Ile Gly His Gln Asp Trp Leu Lys Gly Lys Gln Phe Thr Cys Lys
            195                 200                 205

Val Asn Asn Lys Ala Leu Pro Ser Pro Ile Glu Arg Thr Ile Ser Lys
        210                 215                 220

Ala Arg Gly Gln Ala His Gln Pro Ser Val Tyr Val Leu Pro Pro Ser
225                 230                 235                 240

Arg Glu Glu Leu Ser Lys Asn Thr Val Ser Leu Thr Cys Leu Ile Lys
                245                 250                 255

Asp Phe Phe Pro Pro Asp Ile Asp Val Glu Trp Gln Ser Asn Gly Gln
            260                 265                 270

Gln Glu Pro Glu Ser Lys Tyr Arg Thr Thr Pro Pro Gln Leu Asp Glu
            275                 280                 285

Asp Gly Ser Tyr Phe Leu Tyr Ser Lys Leu Ser Val Asp Lys Ser Arg
290                 295                 300

Trp Gln Arg Gly Asp Thr Phe Ile Cys Ala Val Met His Glu Ala Leu
305                 310                 315                 320

His Asn His Tyr Thr Gln Lys Ser Leu Ser His Ser Pro Gly Lys
                325                 330                 335

<210> SEQ ID NO 83
<211> LENGTH: 335
<212> TYPE: PRT
<213> ORGANISM: Canis familiaris

<400> SEQUENCE: 83

Ala Ser Thr Thr Ala Pro Ser Val Phe Pro Leu Ala Pro Ser Cys Gly
1               5                   10                  15

-continued

```
Ser Thr Ser Gly Ser Thr Val Ala Leu Ala Cys Leu Val Ser Gly Tyr
             20                  25                  30

Phe Pro Glu Pro Val Thr Val Ser Trp Asn Ser Gly Ser Leu Thr Ser
             35                  40                  45

Gly Val His Thr Phe Pro Ser Val Leu Gln Ser Ser Gly Leu Tyr Ser
             50                  55                  60

Leu Ser Ser Met Val Thr Val Pro Ser Ser Arg Trp Pro Ser Glu Thr
 65                  70                  75                  80

Phe Thr Cys Asn Val Ala His Pro Ala Ser Lys Thr Lys Val Asp Lys
                 85                  90                  95

Pro Val Pro Lys Arg Glu Asn Gly Arg Val Pro Arg Pro Pro Asp Cys
                100                 105                 110

Pro Lys Cys Pro Ala Pro Glu Ala Ala Gly Gly Pro Ser Val Phe Ile
                115                 120                 125

Phe Pro Pro Lys Pro Lys Asp Thr Leu Leu Ile Ala Arg Thr Pro Glu
130                 135                 140

Val Thr Cys Val Val Val Asp Leu Asp Pro Glu Asp Pro Glu Val Gln
145                 150                 155                 160

Ile Ser Trp Phe Val Asp Gly Lys Gln Met Gln Thr Ala Lys Thr Gln
                165                 170                 175

Pro Arg Glu Glu Gln Phe Asn Gly Thr Tyr Arg Val Val Ser Val Leu
                180                 185                 190

Pro Ile Gly His Gln Asp Trp Leu Lys Gly Lys Gln Phe Thr Cys Lys
                195                 200                 205

Val Asn Asn Lys Ala Leu Pro Ser Pro Ile Glu Arg Thr Ile Ser Lys
                210                 215                 220

Ala Arg Gly Gln Ala His Gln Pro Ser Val Tyr Val Leu Pro Pro Ser
225                 230                 235                 240

Arg Glu Glu Leu Ser Lys Asn Thr Val Ser Leu Thr Cys Leu Ile Lys
                245                 250                 255

Asp Phe Phe Pro Pro Asp Ile Asp Val Glu Trp Gln Ser Asn Gly Gln
                260                 265                 270

Gln Glu Pro Glu Ser Lys Tyr Arg Thr Thr Pro Pro Gln Leu Asp Glu
                275                 280                 285

Asp Gly Ser Tyr Phe Leu Tyr Ser Lys Leu Ser Val Asp Lys Ser Arg
                290                 295                 300

Trp Gln Arg Gly Asp Thr Phe Ile Cys Ala Val Met His Glu Ala Leu
305                 310                 315                 320

His Asn His Tyr Thr Gln Lys Ser Leu Ser His Ser Pro Gly Lys
                325                 330                 335
```

MONOCLONAL CANINE CD20 ANTIBODIES AND METHODS OF USE

CROSS-REFERENCE TO RELATED APPLICATIONS

This application claims priority to PCT Application Number PCT/US2012/061782, filed Oct. 25, 2012, which claims priority to U.S. Provisional Application No. 61/699,300, filed Sep. 11, 2012, and U.S. Provisional Application No. 61/551,918, filed Oct. 26, 2011.

FIELD OF THE DISCLOSURE

The technology relates to immunogens, and to binding agents that bind the immunogens, like monoclonal antibodies, for identification or isolation of cancer cells that contain the immunogens, or treatment or prevention of cancers containing the cancer cells, especially in dogs.

BACKGROUND INFORMATION

Binding agents like monoclonal antibodies are useful in diagnosis and treatment of diseases like cancer. In canines (dogs), for example, a type of cancer is B cell lymphoma in which uncontrolled B cell proliferation can lead to illness and death. Lymphoma also occurs in humans and may be treated with anti-human CD20 antibodies, like Rituximab, for example. These antibodies, that react with or bind human CD20, generally do not bind canine CD20 (Jubala et al., *Vet Pathol*., July; 42(4):468-76, 2005; Impellizeri et al., *Vet J*., May; 171(3):556-8, 2006; Gravanis et al., *The Oncologist*, December; 15:1335-1343, 2010). Accordingly, binding agents capable of interacting with CD20 on the surface of canine B cells are desired. The technology described herein provides these reagents and therapeutics, as shown below.

SUMMARY OF THE DISCLOSURE

In certain embodiments, this disclosure relates to reagents and methods for preventing and/or treating canine disease conditions (e.g., lymphoma). For example, epitopes of canine CD20 have been identified that may be targeted to deplete canine blood and/or tissues of B cell lymphoma cells. Immunogens have been identified, as described herein, that may be used to induce and/or enhance an immune response (e.g., the production of antibodies) suitable for use in preventing and/or treating these diseases. Nucleic acids encoding the immunogens and the polypeptide/peptide immunogens per se, and methods for making the same are also described. In certain embodiments, the immunogens are or contain particular epitopes of interest such as LIKAPMPYV (SEQ ID NO.: 1) and/or DIHNCD (SEQ ID NO.: 2). These immunogens may be used alone and/or with other immunogens and/or "backbones" (e.g., a canine Fc) to induce and/or enhance an immune response against canine CD20, for example.

In certain embodiments, this disclosure provides binding agents useful in the isolation and/or identification of cells expressing canine CD20 or cells that contain a cell surface protein that reacts with these binding agents (e.g., B cells, B lymphoma cells, canine CD20), and/or treatment and prevention of cancer in a mammal (e.g., a canine). In certain embodiments, the binding agent may be an antibody reactive against canine CD20 expressed on a cell surface. In some embodiments, the one or more binding agents (e.g., an antibody, like a monoclonal antibody) binds to or reacts with canine CD20 at a region thereof which comprises the amino acid sequences, or epitope(s), LIKAPMPYV (SEQ ID NO.: 1) and/or DIHNCD (SEQ ID NO.: 2).

In other embodiments, methods for detecting canine cells using these binding agents are provided. In certain embodiments, cells expressing CD20 on their cell surface (e.g., B cell lymphoma) in an animal (e.g., a canine) can be identified and/or isolated by contacting a test biological sample containing the cells with the binding agent and detecting the binding agent bound to the biological sample or components thereof (e.g., lymphoma cells). In certain embodiments, the method may include comparing the amount of binding in the test biological sample to the amount of binding in a control biological sample, wherein increased binding to the test biological sample relative to the control biological sample may indicate the presence of one or more lymphoma cells in the test biological sample. In some embodiments, the biological sample is canine blood or a needle aspirate. These methods are also provided in an in vivo and/or in vitro format.

In some embodiments, methods for eliminating cells expressing canine CD20 using such binding agents are also provided. Methods for treating one or more disease conditions (e.g., lymphoma) in an animal (e.g., canine) by administering to the animal at least one or more effective doses of binding agent or derivative thereof are also provided. In some embodiments in which the binding agent is a monoclonal antibody, the monoclonal antibody may be administered in a dosage amount of about 1 to about 50 mg/kg of animal body weight, about 1 to about 30 mg/kg, or about 5 to about 30 mg/kg (e.g., about 10 mg/kg). The binding agents may be administered more than once over a period of time. In some embodiments, the binding agent may be administered in conjunction with one or more other agents (e.g., chemotherapeutic agents).

Also provided are kits for using the binding agents to identify or detect polypeptides and/or cells reactive therewith, and/or for using such binding agents to prevent and/or treat disease (e.g., canine lymphoma). The kit may comprise, for example, a binding agent or derivative thereof in any form (e.g., in solution, lyophilized) along with, optionally, instructions for use. Other embodiments will be clear from the descriptions provided herein.

DETAILED DESCRIPTION

Binding Agents

Figure 1:
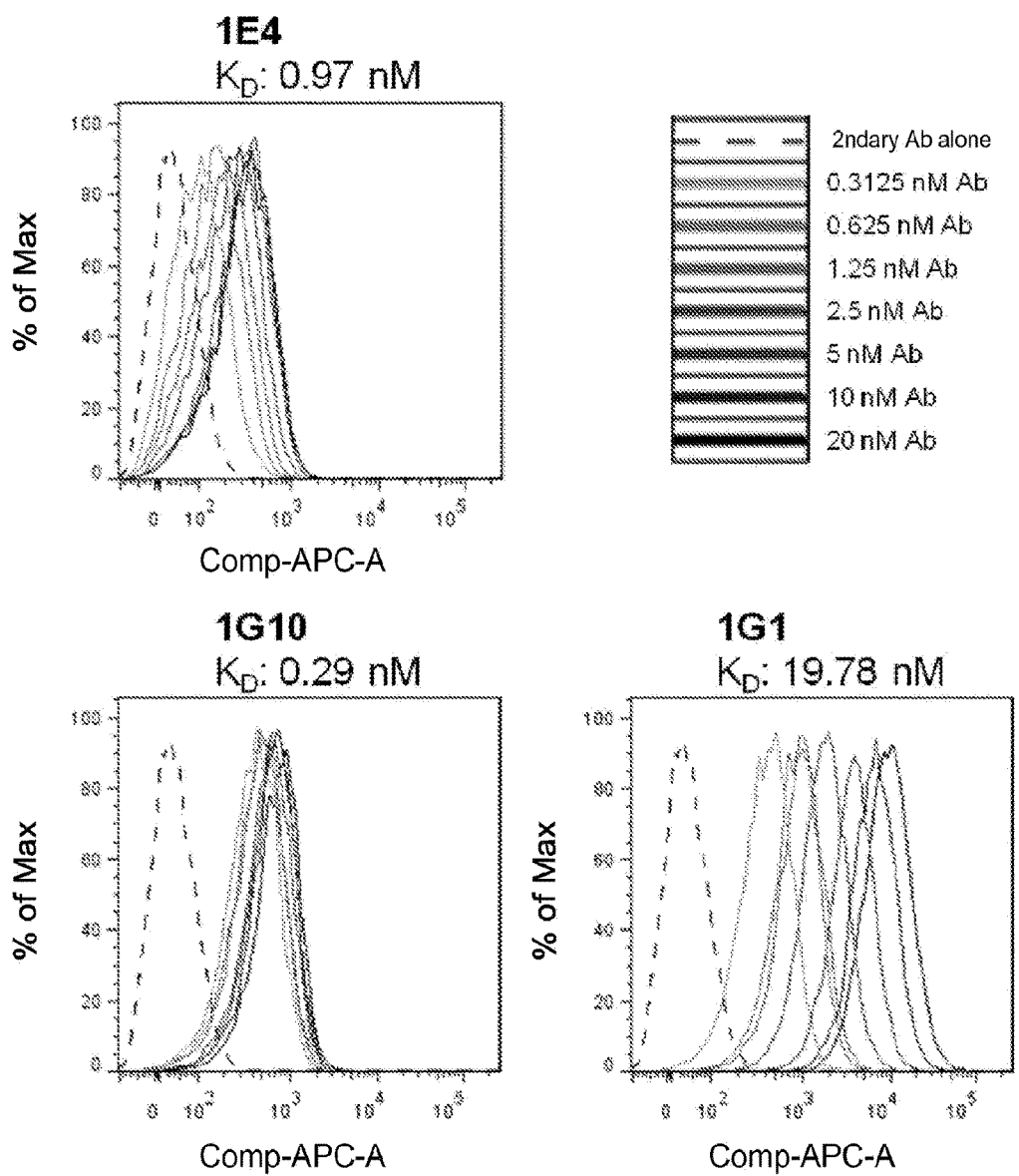
FIG. 1. FACS affinity analysis of binding of monoclonal antibodies to canine B-cell lymphoma cells.

This disclosure relates to binding agents that bind canine CD20 on the surface of cells in vitro and/or in vivo. The binding agents may also bind isolated canine CD20 polypeptide and/or fragments and/or derivatives thereof. Also provided are methods, for diagnosing, treating and/or preventing one or more diseases associated with the existence of cells expressing canine CD20. For instance, the binding agents may be antibodies (e.g., monoclonal antibodies) that may react with and/or bind to the epitopes SEQ ID NOS.: 1 and/or 2. These monoclonal antibodies may comprise any one or more of the amino acid sequences shown in Tables 1 and 4-5, for example, (and/or one or more fragments and/or derivatives thereof) and may be encoded by any one or more of the nucleotide sequences shown therein (and/or one or more fragments and/or derivatives thereof). This disclosure also provides for the use of these monoclonal antibodies to isolate, identify, and/or target cells expressing canine CD20 (e.g., canine B cell lymphoma cells) for inhibition (e.g., cytotoxicity) for the prevention and/or treatment of cancer in animals (e.g., canines). In certain embodiments, these monoclonal antibodies may be reactive against canine CD20 expressed on the surface of cells.

Binding agents generally interact with or bind specifically with a target. For example, the binding agents disclosed herein generally interact specifically with regions of canine CD20 as a target. Binding "specifically" to CD20 means that the amount of binding to CD20 is more than the amount of binding to non-CD20 targets (i.e., there may be background nonspecific binding). Generally, specific binding of binding agents to a protein, for example, may be achieved by binding to a specific sequence of amino acids within a protein target. These sequences may be referred to as epitopes. Molecules containing the epitopes may be used to stimulate binding agents like antibodies and may be referred to as immunogens. The binding agents may also recognize specific 2- and/or 3-dimensional structures as part of the epitope. In one example, monoclonal antibodies disclosed herein may bind to epitopes of canine CD20, like LIKAPMPYV (SEQ ID NO.: 1) and/or DIHNCD (SEQ ID NO.: 2).

The specific interaction or binding of a binding agent with its target is thought to be a type of equilibrium reaction. In one example, the specific binding can be quantified. The quantification may use a dissociation constant, or $K_d$. $K_d$ is known in the art to be a type of equilibrium constant that describes the propensity of, in this case, an antibody to separate from the antigen or epitope to which it has bound. Thus, $K_d$ describes the affinity that an antibody has for an epitope. The lower the $K_d$, the higher is the affinity of a binding agent for its target.

In certain embodiments, the binding agent is a monoclonal antibody selected from the group consisting of 1E4, 1G10, and 1G1, as described herein. The monoclonal antibody may comprise the amino acid sequence of any one or more of SEQ ID NOS.: 3, 6, 9, 11, 13, and/or 15 (e.g., as in Table 1), and/or any one or more fragments and/or derivatives thereof. The antibodies may contain any of the CDR sequences set forth in Table 4. The antibody (e.g., monoclonal antibody) may also be of any suitable isotype or isotype subclass. In certain embodiments, the antibody has a canine IgG subclass of, for example, IgGA, IgGB (e.g., SEQ ID NOS.: 55 or 57; Table 5), IgGC, and/or IgD as described in Tang et al., *Vet Immunol Immunopathol.*, August; 80(3-4):259-70, 2001.

The binding agent may also be a derivative of an antibody (of, for example, the monoclonal antibody 1E4, 1G10, and/or 1G1) such as, for example, a Fab, F(ab')$_2$, Fab' single chain antibody, Fv, single chain, mono-specific antibody, bi-specific antibody, tri-specific antibody, multi-valent antibody, chimeric antibody, canine-human chimeric antibody, canine-mouse chimeric antibody, antibody comprising a canine F$_c$, humanized antibody, human antibody, caninized, CDR-grafted antibody, shark antibody, nanobody (e.g., antibody consisting of a single monomeric variable domain), camelid antibody (e.g., from the Camelidae family) microbody, intrabody (e.g., intracellular antibody), and/or defucosylated antibody and/or derivative thereof. Mimetics of binding agents and/or antibodies are also provided. The binding agent may also comprise a detectable label and/or effector moiety fix ably attached thereto.

Isolated polynucleotides encoding suitable binding agents are also provided. These polynucleotides may comprise, for example, any one or more of SEQ ID NOS.: 4, 5, 7, 8, 10, 12, 14, and/or 16 (e.g., Table 1), and/or any one or more fragments and/or derivatives thereof. In certain embodiments, expression vectors and/or host cells comprising these polynucleotides and/or encoding and/or expressing these polypeptides are also provided.

Compositions comprising these binding agents, polypeptides, peptides, polynucleotides, expression vectors, and/or host cells are also provided in some embodiments. In certain embodiments, the compositions comprise a pharmaceutically acceptable carrier.

The monoclonal antibodies disclosed here (designated as "A" antibodies for this example), that bind to a specific epitope or epitopes, may compete for binding with other antibodies (designated as "B" antibodies for this example) that recognize the same or similar epitopes, or that recognize epitopes that are in proximity to the epitopes recognized by the "A" antibodies (e.g., overlapping epitopes). Competition means that one of the antibodies binds at the expense of the other antibody, or at least inhibits binding of the other antibody to a degree. For example, an "A" antibody that decreases or prevents binding of a "B" antibody is said to compete with "B" for binding. These "B" antibodies are also examples of antibodies that are part of the invention disclosed here. Competition between "A" and "B" antibodies for binding to their epitopes may be measured using so-called competition experiments. Generally, in competition experiments, the binding agents that are to be compared are added to/placed in proximity with, the target to which the binding agents are capable of binding or suspected of binding. The experiments are designed so it is possible to quantify binding of the individual binding agents to the target. Competition is found, for example, when addition of at least one "A" antibody results in binding of a "B" antibody to a lesser degree than if the "A" antibody were not present. In one example, binding agent "A" competes with binding agent "B" for binding to the target. "B" may also compete with "A." The "A" and "B" antibodies may or may not have substantially similar $K_d$'s.

Where the binding agent is an antibody, it may be identified with reference to the nucleotide and/or amino acid sequence corresponding to the variable and/or complementarity determining regions ("CDRs") thereof. For instance, an exemplary binding agent that is, is derived from, or is related to the monoclonal antibody 1E4, 1G10, or 1G1 may comprise a heavy and/or a light chain that each comprise one or more constant and/or variable regions. The variable regions typically comprise one or more CDRs that in large part determine the binding specificity of the antibody. These monoclonal antibodies may be identified by analysis of the nucleotide sequences encoding the variable regions. The monoclonal antibodies may also be identified by analysis of the amino acid sequences of (e.g., which may be encoded by the nucleotide sequences) the variable regions. For instance, exemplary amino acid sequences of the light and heavy chain variable regions of 1E4, 1G10, and 1G1, and exemplary nucleotide sequences encoding the same, are shown below:

TABLE 1

| Description | Sequence |
| --- | --- |
| Light chain variable region ($V_L$) of 1E4 | DVVMTQNPLSLPVSLGDQASISCRSSQSLIYNNGNTYLHWYRQ KPGQSPKLLIYKVSNRFSGVPDRFSGSGSGTDFTLKISRVEAE DLGVYFCSQSTHVPFTFGSGTKLEIK (SEQ ID NO.: 3) |
| Nucleotide sequence encoding SEQ ID NO.: 3 (1E4, $V_L$) | GATGTTGTGATGACCCAAAACCCACTCTCCCTGCCTGTCAGTC TTGGAGATCAAGCCTCCATCTCTTGCAGATCTAGTCAGAGCCT TATATACAATAATGGAAACACCTATTTACATTGGTACCGGCAG AAGCCAGGCCAGTCTCCAAAGCTCCTGATCTACAAAGTTTCCA ACCGATTTTCTGGGGTCCCAGACAGGTTCAGTGGCAGTGGATC AGGGACAGATTTCACACTCAAGATCAGCAGAGTGGAGGCTGAG GATCTGGGAGTTTATTTCTGCTCTCAAAGTACACATGTTCCAT TCACGTTCGGCTCGGGGACAAAGTTGGAAATAAAA (SEQ ID NO.: 4) |
| Codon-optimized nucleotide sequence encoding SEQ ID NO.: 3 (1E4, $V_L$) | GATGTCGTGATGACTCAGAATCCACTGTCCCTGCCTGTGTCCC TGGGCGATCAGGCTTCCATTAGCTGTCGTTCCTCTCAGTCCCT GATCTACAACAATGGTAACACCTACCTGCACTGGTATAGACAG AAGCCCGGCCAGTCCCCTAAGCTGCTGATCTACAAAGTAGTA ATAGGTTCTCAGGAGTCCCAGACCGGTTTTCCGGCAGCGGATC TGGGACCGATTTCACACTGAAAATCTCTAGGGTGGAGGCCGAA GACCTGGGCGTCTACTTTTGTAGTCAGAGCACTCACGTCCCCT TCACCTTCGGCAGCGGAACAAAACTGGAAATCAAG (SEQ ID NO.: 5) |
| Heavy chain variable region ($V_H$) of 1E4 | EVQLVESGGGLVKPGGSLKLSCAASGFTFSDYGMLWVRQAPEK GLEWIAYISSGSSTIYYADRVKGRFTISRDNAKNTLFLQMTSL RSEDTAMYYCSTGTFAYWGQGTPVTVSS (SEQ ID NO.: 6) |
| Nucleotide sequence encoding SEQ ID NO.: 6 (1E4, $V_H$) | GAGGTGCAGCTGGTGGAGTCTGGGGGAGGCTTAGTGAAGCCTG GAGGGTCCCTGAAACTCTCCTGTGCAGCCTCTGGATTCACTTT CAGTGACTATGGAATGCTCTGGGTTCGTCAGGCTCCAGAGAAG GGGCTGGAGTGGATTGCATACATTAGTAGTGGCAGTAGTACCA TCTACTATGCAGACAGAGTGAAGGGCCGATTCACCATCTCCAG AGATAATGCCAAGAACACCCTGTTCCTGCAAATGACCAGTCTG AGATCTGAGGACACGGCCATGTATTACTGTTCAACTGGGACGT TTGCTTACTGGGGCCAAGGGACTCCGGTCACTGTCAGCTCA (SEQ ID NO.: 7) |
| Codon-optimized nucleotide sequence encoding SEQ ID NO.: 6 (1E4, $V_H$) | GAGGTGCAGCTGGTGGAGTCTGGTGGTGGTCTGGTCAAGCCTG GAGGTTCCCTGAAACTGAGTTGTGCCGCATCTGGGTTTACATT CTCTGACTACGGAATGCTGTGGGTGAGGCAGGCACCAGAGAAG GGCCTGGAATGGATCGCTTATATTTCCAGCGGATCTAGTACTA TCTACTATGCAGACAGGGTCAAGGGCCGGTTCACCATTAGCAG AGATAACGCCAAAAATACCCTGTTTCTGCAGATGACATCACTG AGGTCCGAGGATACCGCTATGTATTATTGCTCCACAGGGACTT TTGCTTACTGGGGACAGGGGACACCCGTGACCGTCAGCTCA (SEQ ID NO.: 8) |
| Light chain variable region ($V_L$) of 1G10 | DIVMTQAAPSVPVTPGESVSISCRSNKSLLHRNGNTYLYWFLQ RPGQSPQLLIYRMSNLASGVPDRFSGSGSGTAFTLRISRVEAE DVGVYYCMQHLEFPFTFGGGTKLEIK (SEQ ID NO.: 9) |
| Nucleotide sequence encoding SEQ ID NO.: 9 (1G10, $V_L$) | GATATTGTGATGACTCAGGCTGCACCCTCTGTACCTGTCACTC CTGGAGAGTCAGTATCCATCTCCTGCAGGTCTAATAAGAGTCT CCTGCATCGTAATGGCAACACTTACTTGTATTGGTTTCTGCAG AGGCCAGGCCAGTCTCCTCAGCTCCTGATATATCGGATGTCCA ATCTTGCCTCAGGAGTCCCAGACAGATTCAGTGGCAGTGGGTC AGGAACTGCTTTCACACTGAGAATCAGTAGAGTGGAGGCTGAG GATGTGGGTGTTTATTACTGTATGCAACATCTGGAATTTCCTT TCACGTTCGGCGGGGGGACCAAGCTGGAAATAAAA (SEQ ID NO.: 10) |
| Heavy chain variable region ($V_H$) fo 1G10 | EVQLQQSGPELVKPGASVKISCKASGYTFTDYYMNWVKQSHGK SLEWIGDINPNNGDTSYNQKFKGKAPLTVDKSSSTAYMEVRSL TSEDSAVYFCARGGVLRYPYYYVMDYWGQGTSVTVSS (SEQ ID NO.: 11) |
| Nucleotide sequence encoding SEQ ID NO.: 11 (1G10, $V_H$) | GAGGTCCAGCTGCAACAATCTGGACCTGAGCTGGTGAAGCCTG GGGCTTCAGTGAAGATATCCTGTAAGGCTTCTGGATACACGTT CACTGACTACTACATGAACTGGGTGAAGCAGAGCCATGGAAAG AGCCTTGAGTGGATTGGAGACATTAATCCTAACAATGGTGATA |

TABLE 1 -continued

| Description | Sequence |
|---|---|
| | CTAGCTACAACCAGAAATTCAAGGGCAAGGCCCCCTTGACTGT<br>AGACAAGTCCTCCAGCACAGCCTACATGGAGGTCCGCAGCCTG<br>ACATCTGAGGACTCTGCAGTCTATTTCTGTGCAAGAGGAGGAG<br>TACTACGGTACCCGTATTACTATGTTATGGACTACTGGGGTCA<br>AGGAACCTCAGTCACTGTCAGCTCA (SEQ ID NO.: 12) |
| Light chain variable region (V$_L$) of 1G1 | DIVMTQSQKFMSRSVGDRVSVTCKASQNVGPNVAWYQQRPGQS<br>PKPLIYSASYRYSGVPDRFTGSGSGTDFTLTISNVQSEDLAEY<br>FCQQYNNYPYTFGGGTKLEIK (SEQ ID NO.: 13) |
| Nucleotide sequence encoding SEQ ID NO.: 13 (1G1, V$_L$) | GACATTGTGATGACCCAGTCTCAAAAATTCATGTCCAGATCAG<br>TAGGAGACAGGGTCAGCGTCACCTGCAAGGCCAGTCAGAATGT<br>GGGTCCTAATGTAGCCTGGTATCAACAGAGACCAGGGCAATCT<br>CCTAAACCACTGATTTACTCGGCATCCTACCGGTACAGTGGAG<br>TCCCTGATCGCTTCACAGGCAGTGGATCTGGGACAGATTTCAC<br>TCTCACCATCAGCAATGTGCAGTCTGAAGACTTGGCAGAGTAT<br>TTCTGTCAGCAATATAACAACTATCCGTACACGTTCGGAGGGG<br>GGACCAAGCTGGAAATAAAA (SEQ ID NO.: 14) |
| Heavy chain variable region (V$_H$) of 1G1 | EVQLQQSGAELVRPGASVKLSCTASGFNIKDDYMHWVKQRPEQ<br>GLEWIGWIDPENGHTKYASKFQGKATITADTSSNTAYLQLSSL<br>TSEDTAVYYCTSLRHYYGSSYVSPHYYWGQGTTLTVSS (SEQ ID NO.: 15) |
| Nucleotide sequence encoding SEQ ID NO.: 15 (1G1, V$_H$) | GAGGTTCAGCTGCAGCAGTCTGGGGCTGAGCTTGTGAGGCCAG<br>GGGCCTCAGTCAAGTTGTCCTGCACAGCTTCTGGCTTTAATAT<br>TAAAGACGACTATATGCACTGGGTGAAGCAGAGGCCTGAACAG<br>GGCCTGGAGTGGATTGGATGGATTGATCCTGAGAATGGTCATA<br>CTAAATATGCCTCGAAGTTCCAGGGCAAGGCCACTATAACAGC<br>AGACACATCCTCCAACACAGCCTACCTGCAGCTCAGCAGCCTG<br>ACATCTGAGGACACTGCCGTCTATTACTGTACTTCCCTCCGGC<br>ATTACTACGGTAGTAGCTACGTATCGCCCCATTACTACTGGGG<br>CCAAGGCACCACTCTCACTGTCAGCTCA (SEQ ID NO.: 16) |

Any of the amino acids shown in Table 1 (and/or any one or more fragments and/or derivatives thereof) may also be substituted by any other amino acid as desired by one of ordinary skill in the art. For example, one of skill in the art may make conservative substitutions by replacing particular amino acids with others as shown in Table 7 below. Exemplary amino acids that may be substituted may include, for example, residues 26, 28, 33, and/or 34 of SEQ ID NO.: 9 (1G10 light chain variable region); residues 55 and/or 56 of SEQ ID NO.: 11 (1G1 heavy chain variable region); and/or residues 52, 53, 55 and/or 56 of SEQ ID NO.: 15 (1G1 heavy chain variable region), which may be substituted with any other amino acid including but not limited to the conservative substitutions shown in Table 7 below. Nucleotide sequences encoding the conservative amino acid substitutions may be designed using the genetic code as set forth in Table 6. Examples of such substituted amino acid sequences include, for instance:
DIVMTQAAPSVPVTPGESVSISCRSXKXLLHRXXN-TYLYWFLQRPGQSPQLLIYR MSNLASGVPDRF-SGSGSGSGTAFTLRISRVEAEDVGVYYCMQHLEFP-FTFGGGTKLE IK (SEQ ID NO.: 17) where X is any amino acid (modification of 1G10 light chain variable region indicated by SEQ ID NO.: 9);
EVQLQQSGPELVKPGASVKISCKASGYTFTDYYMN-WVKQSHGKSLEWIGDINPN XXDTSYNQKFKGKA-PLTVDKSSSTAYMEVRSLTSEDSAVYFCARGGVLRY-PYY YVMDYWGQGTSVTVSS (SEQ ID NO.: 18) where X is any amino acid (modification of 1G10 heavy chain variable region indicated by SEQ ID NO.: 11; and,
EVQLQQSGAELVRPGASVKLSCTASGFNIKDDYMH-WUKQRPEQGLEWIGWIXX EXXHTKYASKFQGKATI-TADTSSNTAYQLSSLTSEDTAVYYCTSLRHYYGSSY VSPHYYWGQGTTLTVSS (SEQ ID NO.: 19) where X is any amino acid (modification of 1G1 heavy chain variable region indicated by SEQ ID NO.: 15.

Any of the amino acid sequences shown in Table 1, and/or any fragments and/or derivatives thereof may also be combined with any other variable region and/or CDR in any order and/or combination to form hybrid and/or fusion binding agents and/or inserted into other heavy and/or light chain variable regions using standard techniques. These may be used in conjunction with any constant regions (e.g., as in Table 5).

CDRs (complementarity-determining regions) are amino acid sequences from antibodies that are, at least in part, responsible for binding of an antibody to a specific target. It is understood by those of skill in the art that CDRs may be identified using any of several techniques and/or schemes. CDRs of the binding agents shown herein may be identified using any of these techniques. For instance, one of ordinary skill in the art may identify CDRs using the Kabat Numbering Scheme, the Chothia Numbering Scheme, the Enhanced Chothia Numbering Scheme, and/or any of the available CDR Definition Schemes (e.g., AbM, contact definition, and/or as described by MacCullum, et al., *J. Mol. Biol.*, 262(5):732-745, 1996. A summary of various schemes, in part based on, for example, Kabat et al., "Sequences of Proteins of Immunological Interest," 5th Ed., Public Health Service, National Institutes of Health, Bethesda, Md., NIH publication No. 91-3242 (1991), and Al-Lazikani et al., "Standard conformations for the canonical structures of immunoglobulins," J. Mol. Biol. 273:927-948, 1997, is provided in Table 2 below:

TABLE 2

| CDR Loop* | Kabat | AbM | Chothia | Contact |
|---|---|---|---|---|
| L1 | L24 - - - L34 | L24 - - - L34 | L24 - - - L34 | L30 - - - L36 |
| L2 | L50 - - - L56 | L50 - - - L56 | L50 - - - L56 | L46 - - - L55 |
| L3 | L89 - - - L97 | L89 - - - L97 | L89 - - - L97 | L89 - - - L96 |
| H1 | H31 - - - H35B (Kabat Numbering) | H26 - - - H35B | H26 - - - H32 . . . 34 | H30 - - - H35B |
| H1 | H31 - - - H35 (Chothia Numbering) | H26 - - - H35 | H26 - - - H32 | H30 - - - H35 |
| H2 | H50 - - - H65 | H50 - - - H58 | H52 - - - H56 | H47 - - - H58 |
| H3 | H95 - - - H102 | H95 - - - H102 | H95 - - - H102 | H93 - - - H101 |

*L = light chain; H = heavy chain

CDRs may also be identified by following a set of rules such as those set forth in Table 3 below (as described at http://www.bioinf.org.uk/abs/#cdrid):

TABLE 3

| CDR*/Feature | Typical Characteristic of Feature** |
|---|---|
| CDR-L1 | |
| Start | approximately residue 24 |
| Residues before | typically Cys |
| Residues after | typically Trp (e.g., Trp-Tyr-Gln, Trp-Leu-Gln, Trp-Phe-Gln, Trp-Tyr-Leu) |
| Length | 10 to 17 residues |
| CDR-L2 | |
| Start | typically 16 residues after the end of L1 |
| Residues before | typically Ile-Tyr, Val-Tyr, Ile-Lys, or Ile-Phe |
| Length | typically seven (7) residues |
| CDR-L3 | |
| Start | typically 33 residues after end of L2 |
| Residues before | typically Cys |
| Length | typically Phe-Gly-X-Gly |
| Residues after | 7 to 11 residues |
| CDR-H1 | |
| Start | Approximately residue 26 (typically four (4) residues after a Cys) (Chothia/AbM definition); Kabat definition starts 5 residues later |
| Residues before | typically Cys-X-X-X |
| Residues after | typically Trp (e.g., Trp-Val, Trp-Ile, Trp-Ala) |
| Length | 10 to 12 residues (AbM definition); Chothia definition excludes the last four (4) residues |
| CDR-H2 | |
| Start | typically 15 residues after the end of Kabat/AbM definition of CDR-H1 |
| Residues before | typically Leu-Glu-Trp-Ile-Gly |
| Residues after | typically Lys/Arg-Leu/Ile/Val/Phe/Thr/Ala-Thr/Ser/Ile/Ala |
| Length | Kabat definition 16 to 19 residues; AbM (and recent Chothia) definition 9 to 12 residues |
| CDR-H3 | |
| Start | typically 33 residues after end of CDR-H2 (typically two (2) residues following a Cys) |
| Residues before | typically Cys-X-X (typically Cys-Ala-Arg) |
| Residues after | typically Trp-Gly-X-Gly |
| Length | typically 3 to 25 residues |

*L = light chain; H = heavy chain; **X = any amino acid

These systems for identifying CDRs are merely exemplary and others may be suitable, as would be understood by one of ordinary skill in the art. CDRs thus identified may be used to identify suitable binding agents. For instance, equivalents of one or more of the monoclonal antibodies 1E4, 1G10, and/or 1G1 may be binding agents comprising the amino acid sequences. Such CDRs may also be combined with one another in any order and/or combination to form hybrid and/or fusion binding agents and/or inserted into the other heavy and/or light chain variable regions using standard techniques. The amino acid sequences shown in Table 1, and/or any one or more fragments and/or derivatives thereof, may be encoded by any of several nucleic acid sequences. These nucleic acid sequences may also be used to identify and/or prepare (e.g., as nucleic acid molecules) suitable binding agents. For example, one of ordinary skill in the art may devise nucleotide sequences encoding any such amino acid sequences with reference to any one or more of Tables 1-7 herein. Exemplary nucleotide sequences encoding the light chain variable regions of 1E4, 1G10, and 1G1 may be those shown in Table 1. Any of the nucleotide sequences shown in Table 1, and/or fragments and/or derivatives thereof, may be combined with one another in any order and/or combination to encode hybrid and/or fusion binding agents and/or inserted into the other nucleic acid sequences encoding light and/or heavy chain variable regions (and/or fragments and/or derivatives thereof). Exemplary fragments may be, for example, any nucleic acid sequence encoding any of the amino acid sequences shown in Table 1, and/or any fragment and/or derivative thereof (e.g., one or more CDRs thereof). Putative CDRs of the monoclonal antibodies 1E4, 1G10 and 1G1 are listed in Table 4. These CDRs were identified using the schemes set forth in, Kabat et al., "Sequences of Proteins of Immunological Interest," 5th Ed., Public Health Service, National Institutes of Health, Bethesda, Md., NIH publication No. 91-3242 (1991), and Al-Lazikani et al., "Standard conformations for the canonical structures of immunoglobulins," J. Mol. Biol. 273:927-948, 1997.

TABLE 4

| CDR | Kabat CDRs (Kabat et al. 1991) | Chothia CDRs (Al-Lazikani et al. 1997) |
|---|---|---|
| 1E4 CDRH1 | DYGML (SEQ ID NO.: 20) | GFTFSDY (SEQ ID NO.: 21) |
| 1E4 CDRH2 | YISSGSSTIYYADRVKG (SEQ ID NO.: 22) | SSGSST (SEQ ID NO.: 23) |
| 1E4 CDRH3 | GTFAY (SEQ ID NO.: 24) | GTFAY (SEQ ID NO.: 24) |
| 1E4 CDRL1 | RSSQSLIYNNGNTYLH (SEQ ID NO.: 25) | SQSLIYNNGNTY (SEQ ID NO.: 26) |
| 1E4 CDRL1 N33 to K | RSSQSLIYNKGNTYLH (SEQ ID NO.: 70) | SQSLIYNKGNTY (SEQ ID NO.: 71) |
| 1E4 CDRL1 G34 to K | RSSQSLIYNNKNTYLH (SEQ ID NO.: 72) | SQSLIYNNKNTY (SEQ ID NO.: 73) |
| 1E4 CDRL1 G34 to Q | RSSQSLIYNNKNTYLH (SEQ ID NO.: 74) | SQSLIYNNQNTY (SEQ ID NO.: 75) |

TABLE 4 -continued

| CDR | Kabat CDRs (Kabat et al. 1991) | Chothia CDRs (Al-Lazikani et al. 1997) |
|---|---|---|
| 1E4 CDRL1 G34 to A | RSSQSLIYNNQNTYLH (SEQ ID NO.: 76) | SQSLIYNNANTY (SEQ ID NO.: 77) |
| 1E4 CDRL2 | KVSNRFS (SEQ ID NO.: 27) | KVS (SEQ ID NO.: 28) |
| 1E4 CDRL3 | SQSTHVPFT (SEQ ID NO.: 29) | STHVPF (SEQ ID NO.: 30) |
| 1G1 CDRH1 | DDYMH (SEQ ID NO.: 31) | GFNIKDD (SEQ ID NO.: 32) |
| 1G1 CDRH2 | WIDPENGHTKYASKFQG (SEQ ID NO.: 33) | DEPNGH (SEQ ID NO.: 34) |
| 1G1 CDRH3 | LRHYYGSSYVSPHYY (SEQ ID NO.: 35) | LRHYYGSSYVSPHYY (SEQ ID NO.: 36) |
| 1G1 CDRL1 | KASQNVGPNVA (SEQ ID NO.: 37) | SQNVGPN (SEQ ID NO.: 38) |
| 1G1 CDRL2 | SASYRS (SEQ ID NO.: 39) | SAS (SEQ ID NO.: 40) |
| 1G1 CDRL3 | QQYNNYPYT (SEQ ID NO.: 41) | YNNYPY (SEQ ID NO.: 42) |
| 1G10 CDRH1 | DYYMN (SEQ ID NO.: 43) | GYTFTDY (SEQ ID NO.: 44) |
| 1G10 CDRH2 | DINPNNGDTSYNQKFKG (SEQ ID NO.: 45) | NPNNGD (SEQ ID NO.: 46) |
| 1G10 CDRH3 | GGVLRYPYYYVMDY (SEQ ID NO.: 47) | GGVLRYPYYYVMDY (SEQ ID NO.: 48) |
| 1G10 CDRL1 | RSNKSLLHRNGNTYLY (SEQ ID NO.: 49) | NKSLLHRNGNTY (SEQ ID NO.: 50) |
| 1G10 CDRL2 | RMSNLAS (SEQ ID NO.: 51) | RMS (SEQ ID NO.: 52) |
| 1G10 CDRL3 | MQHLEFPFT (SEQ ID NO.: 53) | HLEFPF (SEQ ID NO.: 54) |

In some embodiments, the binding agent may comprise the amino acid sequences set forth in Table 4 above. Subgroups of these combinations and/or other combinations of the CDRs shown in Table 4 may also be suitable, as would be understood by those of skill in the art. In one example, various combinations of the above CDRs may be used to provide caninized antibodies.

The variable region sequences described herein (which may comprise fragments and/or derivatives thereof), including but not limited to the amino acid sequences shown in Table 1 (and/or fragments and/or derivatives thereof) and/or the nucleotide sequences shown in Table 1 (and/or fragments and/or derivatives thereof) may be used in combination with one or more amino acid sequences and/or nucleotide sequences encoding one or more constant chains (and/or a fragment and/or derivatives thereof) of an antibody molecule. For instance, the variable region amino acid sequences shown in Table 1 may be joined to the constant regions of any antibody molecule of the same or a different species (e.g., human, goat, rat, sheep, chicken) of that from which the variable region amino acid sequence was derived.

Deamidation of asparagine residues to aspartic acid or isoaspartic acid is a common post-translational modification to proteins. Deamidation may occur with higher frequency when the asparagine is part of an asparagine-glycine dipeptide (Asp-Gly or N-G; the "NG" sequence). Deamidation may have detrimental effects on proteins. In one example, deamidation may potentially cause a change in the three-dimensional structure of a protein. In another example, for an antibody, deamidation in a region that affects binding to an antigen (e.g., variable regions and/or CDRs) may potentially cause lower or loss of antibody binding to the antigen.

Accordingly, it may be beneficial to substitute amino acid residues potentially susceptible to post-translational deamidation with those less or not susceptible. In one example, asparagine 33 (N33) and/or glycine 34 (G34) of SEQ ID NO.: 3 (light chain variable region ($V_L$) of 1E4) may be substituted to modify the NG sequence (see, e.g., SEQ ID NOS. 71, 73, 75 and 77). SEQ ID NO.: 3 is shown below, with N33 and G34 (an NG sequence) underlined:

(SEQ ID NO.: 3)
DVVMTQNPLSLPVSLGDQASISCRSSQSLIYN<u>NG</u>NTYLHWYRQKPG
QSPKLLIYKVSNRFSGVPDRFSGSGSGTDFTLKISRVEAEDLGVYF
CSQSTHVPFTFGSGTKLEIK

N33 and/or G34 may be substituted by, for example, any amino acid such as alanine (A), glutamic acid (E), phenylalanine (F), histidine (H), isoleucine (I), lysine (K), leucine (L), methionine (M), proline (P), glutamine (Q), arginine (R), threonine (T), valine (V), and/or tyrosine (Y), in any combination. In some embodiments, N33 may be substituted by, for example, alanine (A), glutamic acid (E), phenylalanine (F), histidine (H), isoleucine (I), lysine (K), leucine (L), proline (P), glutamine (Q), arginine (R), threonine (T), valine (V) or tyrosine (Y). In some embodiments, G34 may be substituted by, for example, alanine (A), glutamic acid (E), phenylalanine (F), histidine (H), isoleucine (I), lysine (K), leucine (L), proline (P), glutamine (Q), arginine (R), valine (V), tryptophan (W) or tyrosine (Y) in any combination.

In one embodiment, N33 (of, e.g., SEQ ID NO.: 9) may be substituted by lysine (K) (N33K substitution). In particular embodiments, G34 (of, e.g., SEQ ID NO.: 9), may be substituted by lysine (K) (G34K), glutamine (Q) (G34Q), or alanine (A) (G34A). In some embodiments, the substitutions may include N33K and any of G34K, G34Q, or G34A. Other substitutions may also be suitable as would be understood by one of ordinary s kill in the art.

In other embodiments, asparagine 33 (N33) and/or glycine 34 (G34) of SEQ ID NO.: 9 (light chain variable region ($V_L$) of 1G10), asparagine 55 (N55) and/or glycine 56 (G56) of SEQ ID NO.: 11 (heavy chain variable region ($V_H$) of 1G10), or asparagine 55 (N55) and/or glycine 56 (G56) of SEQ ID NO.: 15 (heavy chain variable region ($V_H$) of 1G1) may be substituted by any suitable amino acid. In another example, one or more of asparagines 103 (N103), 183 (N183) and/or 270 (N270), and/or glycines 104 (G104), 184 (G184) and/or 271 (G271) of SEQ ID NO.: 57 (canine IgGB heavy chain constant region) may be substituted by any suitable amino acid. Additional information regarding certain substitutions is described and tested in the Examples. And other substitutions may also be suitable, as may be determined by one of ordinary skill in the art.

The constant regions may be derived from any of, for example, human (e.g., IgG (IgG1, IgG2, IgG3, IgG4), IgM, IgA (IgA1 and IgA2), IgD, and IgE), canine (e.g., IgG (IgGA, IgGB, IgGC, IgGD) IgA, IgD, IgE, and IgM), chicken (e.g., IgA, IgD, IgE, IgG, IgM, IgY), goat (e.g., IgG), mouse (e.g., IgA, IgG, IgD, IgE, IgM), pig (e.g., IgA, IgG. IgD, IgE, IgM), rat (e.g., IgA, IgG, IgD, IgE, IgM), feline (e.g., IgA, IgD, IgE, IgG. IgM) and/or a fragment and/or derivative thereof (e.g., as chimeric antibodies). For example, one or more of the amino acid sequences of Table 1 and/or Table 4 may be adjoined or associated with a non-canine variable and/or constant region (e.g., human) to produce a chimeric antibody. A binding agent may, for example, comprise an amino acid sequence of any of those shown in Table 1 (and/or fragments and/or derivatives thereof) and, for example, a canine antibody constant region. Exemplary amino acid and nucleotide sequences of canine IgGB light and heavy chain constant regions that may be utilized as described herein are shown below in Table 5:

TABLE 5

| Description | Sequence |
|---|---|
| Amino acid sequence of canine light chain constant region | RNDAQPAVYLFQPSPDQLHTGSASVVCLLNSFYPKDINVKWKV DGVIQDTGIQESVTEQKDDSTYSLSSTLTMSSTEYLSHELYSC EITHKSLPSTLIKSFQRSECQRVD (SEQ ID NO.: 55) |
| Codon-optimized nucleotide sequence encoding SEQ ID NO.: 55 | CGTAACGACGCCCAGCCTGCCGTGTATCTGTTCCAGCCCTCCC CCGATCAGCTGCATACCGGGTCCGCCTCAGTGGTGTGCCTGCT GAACAGTTTCTACCCCAAGGACATCAATGTGAAGTGGAAAGTG GACGGCGTCATCCAGGATACTGGCATCCAGGAGAGCGTCACCG AACAGGACAAAGATTCAACATATTCCCTGTCCAGCACCCTGAC AATGTCTAGTACTGAGTACCTGAGCCACGAACTGTATTCTTGC GAGATTACCCATAAGAGCCTGCCATCCACCCTGATTAAGAGTT TCCAGCGTTCCGAATGCCAGAGAGTCGAT (SEQ ID NO.: 56) |
| Amino acid sequence of canine light chain constant region N2 to T | RTDAQPAVYLFQPSPDQLHTGSASVVCLLNSFYPKDINVKWKV DGVIQDTGIQESVTEQKDSTYSLSSTLTMSSTEYLSHELYSC EITHKSLPSTLIKSFQRSECQRVD (SEQ ID NO.: 78) |
| Amino acid sequence of canine light chain constant region N30 to S | RNDAQPAVYLFQPSPDQLHTGSASVVCLLSSFYPKDINVKWKV DGVIQDTGIQESVTEQKDSTYSLSSTLTMSSTEYLSHELYSC EITHKSLPSTLIKSFQRSECQRVD (SEQ ID NO.: 79) |
| Amino acid sequnce of canine light chain constant region N2 to T, N30 to S | RTDAQPAVYLFQPSPDQLHTGSASVVCLLSSFYPKDINVKWKV DGVIQDTGIQESVTEQKDSTYSLSSTLTMSSTEYLSHELYSC EITHKSLPSTLIKSFQRSECQRVD (SEQ ID NO.: 80) |
| Amino acid sequence of canine IgGB heavy chain constant region | ASTTAPSVFPLAPSCGSTSGSTVALACLVSGYFPEPVTVSWNS GSLTSGVHTFPSVLQSSGLYSLSSMVTVPSSRWPSETFTCNVA HPASKTKVDKPVPKRENGRVPRPPDCPKCPAPEMLGGPSVFIF PPKPKDTLLIARTPEVTCVVVDLDPEDPEVQISWFVDGKQMQT AKTQPREEQFNGTYRVVSVLPIGHQDWLKGKQFTCKVNNKALP SPIERTISKARGQAHQPSVYVLPPSREELSKNTVSLTCLIKDF FPPDIDVEWQSNGQQEPESKYRTTPPQLKEDGSYFLYSKLSVD KSRWQRGDTFICAVHHEALHNHYTQKSLSHSPGK (SEQ ID NO.: 57) |
| Codon-optimized nucleotide sequence encoding SEQ ID NO.: 57 | GCGTCAACTACCGCTCCCTCCGTCTTCCCTCTGGCTCCTTCAT GTGGTTCAACAAGTGGCAGTACCGTCGCCCTGGCTTGCCTGGT GTCAGGGTACTTCCCTGAGCCAGTCACCTGTGTCCTGGACAGC GGGTCTCTGACAAGTGGTGTCCACACTTTTCCTTCAGTGCTGC AGTCCAGCGGTCTGTATTCCCTGTCTAGTATGGTCACTGTGCC ATCATCCAGATGGCCCAGCGAAACTTTCACCTGTAACGTGGCA CATCCAGCCTCTAAGACCAAAGTGGACAAGCCCGTGCCTAAAC GAGAGAATGGAAGGGTGCCTCGACCACCTGATTGCCCAAAGTG TCCAGCACCAGAAATGCTGGGAGGACCATCCGTGTTCATCTTT CCACCCAAGCCTAAAGACACACTGCTGATTGCTAGGACCCCAG AGGTGACATGCGTGGTCGTGGACCTGGATCCCGAGGACCCTGA AGTCCAGATCAGCTGGTTCGTGGATGGGAAGCAGATGCAGACA GCAAAAACTCAGCCAAGGGAGGAACAGTTTAATGGTACTTACC GGGTCGTGTCTGTGCTGCCCATTGGCCACCAGGACTGGCTGAA GGGAAAACAGTTTACCTGCAAGGTGAACAACAAGGCTCTGCCT TCCCCAATCGAGCGAACAATTAGCAAGGCTCGTGGCCAGGCAC ATCAGCCCAGCGTCTACGTGCTGCCTCCATCCCGAGAGGAACT GAGCAAGAACACTGTGTCTCTGACCTGTCTGATCAAAGATTTC TTTCCCCCTGACATTGATGTGGAGTGGCAGTCTAATGGACAGC AGGAGCCTGAGAGTAAGTATCGGACCACACCACCCCAGCTGGA CGAAGATGGCAGTTACTTCCTGTATAGTAAGCTGTCAGTGGAC AAATCCAGATGGCAGCGCGGAGAACCTTCATCTGTGCCGTGA TGCACGAAGCACTGCACAATCACTACACACAGAAGTCACTGAG CCACTCTCCAGGGAAA (SEQ ID NO.: 58) |

One of ordinary skill in the art would understand that the constant regions of binding agents that are antibodies may be encoded by SEQ ID NO.: 56 and/or 58 and/or derivative nucleotide sequences thereof. The constant regions of the binding agents may comprise the amino acid sequence of SEQ ID NO.: 55, 78, 79, 80 and/or 57, and/or derivative amino acid sequences thereof. In one example, nucleotide sequences encoding the antibodies are constructed into a vector system, and then expressed in host cells. In one example, the host cells are cultured cells. In one example, the vector system is used in mammalian cultured cells under conditions where the antibodies are expressed. Example 2 describes an example of this.

In some applications, the binding agents may bind canine CD20 but have altered ability to bind Fc receptors (e.g., CD16) as compared to standard binding agents. In one example, the binding agents are antibodies that have modified glycosylation patterns. IgG molecules, for example, typically contain N-linked oligosaccharides. Some IgG molecules contain a biantennary complex-type oligosaccharide linked to the antibody heavy chain. In human IgG, the oligosaccharide is generally linked to an asparagine residue at position 297 (N297) of the heavy chain (in the constant/Fc region of the antibody heavy chain). Generally, a fucose is attached to the GLcNAC residue in the oligosaccharide that is nearest to N297. Absence of the fucose may enhance the ability of the antibodies to mediate antibody-dependent cellular cytotoxicity (ADCC). Presumably, absence/removal of the fucose enhances the ability of the antibody to interact with Fc receptors. Antibodies of this type may be referred to as "defucosylated". Defucosylated antibodies may be produced using techniques described herein and/or that may be known in the art. In some embodiments, a nucleic acid sequence encoding an antibody may be expressed in a cell line that has modified glycosylation abilities (e.g., deleted, modified or lesser amount of fucosyl transferase) and fail to add the typical fucose moieties. A variety of these cell lines are known. In some embodiments, the antibodies disclosed herein bind to canine CD20 but contain defucosylated oligosaccharides. In one embodiment, the anti-canine CD20 antibody may contain a canine IgGB heavy chain constant region. In some embodiments, the fucose moiety typically attached to the GLcNAC nearest N183 in canine IgGB heavy chain constant region (SEQ ID NO.: 57) is absent. Other techniques may also be used to alter the typical fucosylation of antibodies and may be suitable, as would be understood by one of ordinary skill in the art.

The binding agents (e.g., antibodies) may include other modifications that may result in decreased interaction with Fc receptors (e.g., CD16). For instance, alternative or additional amino acid substitutions may be made to the antibody molecules described herein. In one embodiment, canine IgGB heavy chain constant region (e.g., of SEQ ID NO.: 57) may be substituted at one or both of amino acid residues M120 and L121. In certain embodiments, either or both of these residues may be substituted by alanine (A) or proline (P). In one embodiment, M (methionine) at position 120 was substituted by P (proline) and L (leucine) at position 121 was substituted by A (alanine), as shown below:

(SEQ ID NO.: 81)
ASTTAPSVRPLAPSCGSTSGSTVALACLVSGYFPEPVTVSWNSGSLTS

GVHTFPSVLQSSGLYSLSSMVTVPSSRWPSETFTCNVAHPASKTKVDK

PVPKRENGRVPRPPDCPKCPAPEPAGGPSVFIFPPKPKDTLLIARTPE

VTCVVVDLDPEDPEVQISWFVDGKQMQTAKTQPREEQFNGTYRVVSVL

PIGHQDWLKGKQFTCKVNNKALPSPIERTISKARGQAHQPSVYVLPPS

REELSKNTVSLTCLIKDFFPPDIDVEWQSNGQQEPESKYRTTPPQLDE

DGSYFLYSKLSVDKSRWQRGDTFICAVMHEALHNHYTQKSLSHSPGK.

In studies to characterize canine IgGB containing M120P and L121A, binding to CD16a was reduced as compared to canine IgGB that did not contain the substitutions (i.e., the sequence as shown in SEQ ID NO.: 57). Canine IgGA heavy chain was used as negative control, as it minimally or does not bind CD16a in our hands. We have also found that canine IgGD heavy chain also minimally or does not bind CD16a, while canine IgGB and IgGC heavy chains do bind CD16a (also, in B cell depletion experiments, as described in Example 3 and FIG. 6, 1E4-cIgGB and 1E4-cIgGC molecules did deplete B cells, while a 1E4-cIgGA molecule did not). Measured binding of the molecule containing M120P and L121A was similar to the background level of binding measured for the IgGA molecule.

In one embodiment, the canine IgGB heavy chain constant region (e.g., of SEQ ID NO.: 57) N (asparagine) at position 183 was substituted by A, as shown below:

(SEQ ID NO.: 82)
ASTTAPSVFPLAPSCGSTSGSTVALACLVSGYFPEPVTVSWNSGSLTS

GNGTFPSVLQSSGLYSLSSMVTVPSSRWPSETFTCNVAHPASKTKVDK

PVPKRENGRVPRPPDCPKCPAPEMLGGPSVFIFPPKPKDTLLIARTPE

VTCVVVDLDPEDPEVQISWFVDGKQMQTAKTQPREEQFAGTYRVVSVL

PIGHQDWLKGKQFTCKVNNKALPSPIERTISKARGQAHSPSVYVLPPS

REELSKNTVSLTCLIKDFFPPDIDVEWQSNGQQEPESKYRTTPPQKDE

DGSYFLYSKLSVDKSRWQRGDTFICAVMHEALHNHYTQKSLSHSPGK;

In studies to characterize canine IgGB containing the N183A substitution, binding to CD16a was reduced as compared to canine IgGB that did not contain the substitutions (i.e., the sequence as shown in SEQ ID NO.: 57). Canine IgGA heavy chain was used as negative control. Measured binding to CD16a of the molecule containing the N183A substitution was similar to the background level of binding measured for the IgGA molecule.

In one embodiment, the canine IgGB heavy chain constant region (e.g., of SEQ ID NO.: 57) M at position 120 was substituted by A and L at position 121 was substituted by A, as shown below:

(SEQ ID NO.: 83)
ASTTAPSVFPLAPSCGSTSGSTVALACLVSGYFPEPVTVSWNSGSLTSG

VHTFPSVLQSSGLYSLSSMVTVPSSRWPSETFTCNVAHPASKTKVDKPV

PKRENGRVPRPPDCPKCPAPEAAGGPSVFIFPPKPKDTLLIARTPEVTC

VVVDLDPEDPEVQISWFVDGKQMQTAKTQPREEQFNGTYRVVSVLPIGH

QDWLKGKQFTCKVNNKALPSPIERTISKARGQAHQPSVYVLPPSREELS

KNTVSLTCLIKDFFPPDIDVEWQSNGQQEPESKYRTTPPQLDEDGSYFL

YSKLSVDKSRWQRGDTFICAVMHEALHNKYTQKSLSKSPGK;

In studies to characterize canine IgGB containing M120A and L121A, binding to CD16a was reduced as compared to canine IgGB that did not contain the substitutions (i.e., the sequence as shown in SEQ ID NO.: 57). Canine IgGA heavy chain was used as negative control. Measured binding to CD16a of the molecule containing M120A and L121A was decreased compared to binding of IgGB that does not contain the substitutions. However, binding to CD16A of the M120A- and L121A-containing molecule was not reduced as much as for binding of the M120P and L121A molecule, or as much as for binding of the N183A molecule.

In addition to the above molecules, the canine IgGB heavy chain constant region (SEQ ID NO.: 57) may have other amino acid substitutions, for example, at one or both of M120 and L121. In one embodiment, the molecule may have a M120A substitution. In one embodiment, the molecule may have a L121A substitution. Other substitutions of M120 and/or L121, by A and/or P may be possible. In addition, any of these substitutions may be combined with the N183A substitution. Other modifications may also be suitable, as would be understood by one of ordinary skill in the art. Mixtures of antibodies having one or more of such modifications may also be suitable for various applications.

As described above, in some embodiments, binding agents may be antibodies. The term "antibody" or "antibodies" may refer to whole or fragmented antibodies in unpurified or partially purified form (e.g., hybridoma supernatant, ascites, polyclonal antisera) or in purified form. A "purified" antibody may be one that is separated from at least about 50% of the proteins with which it is initially found (e.g., as part of a hybridoma supernatant or ascites preparation). A purified antibody may be one that is separated from at least about 60%, 75%, 90%, or 95% of the proteins with which it is initially found. Suitable derivatives may also be fragments (e.g., Fab, F(ab')$_2$ or single chain antibodies, like Fv, for example). The antibodies may be of any suitable origin or form including, for example, murine (e.g., produced by murine hybridoma cells), or expressed as caninized antibodies, chimeric antibodies, canine antibodies, and the like.

Methods of preparing and utilizing various types of antibodies are well-known to those of skill in the art and would be suitable in practicing the present invention (see, for example, Harlow, et al. *Antibodies: A Laboratory Manual*, Cold Spring Harbor Laboratory, 1988; Harlow, et al., *Using Antibodies: A Laboratory Manual*, Portable Protocol No. 1, 1998: Kohler and Milstein, *Nature*, 256:495, 1975; Jones et al., *Nature*, 321:522-525, 1986; Riechmann et al., *Nature*, 332:323-329, 1988; Presta, *Curr. Op. Struct. Biol.*, 2:593-596, 1992; Verhoeyen et al., *Science*, 239:1534-1536, 1988; Hoogenboom et al. *J. Mol. Biol.*, 227:381, 1991; Marks et al., *J. Mol. Biol.*, 222:581, 1991; Cole et al., Monoclonal Antibodies and Cancer Therapy, Alan R. Liss, p. 77, 1985; Boerner et al., *J. Immunol.*, 147(1):86-95, 1991; Marks et al., *Bio/Technology* 10, 779-783, 1992: Lonberg et al., *Nature* 368:856-859, 1994; Morrison, *Nature* 368:812-13, 1994; Fishwild et al., *Nature Biotechnology* 14, 845-51, 1996; Neuberger, *Nature Biotechnology* 14, 826, 1996; Lonberg and Huszar, *Intern. Rev. Immunol.* 13:65-93, 1995; as well as U.S. Pat. Nos. 4,816,567, 5,545,807, 5,545,806, 5,569,825, 5,625,126, 5,633,425, and 5,661,016). In certain applications, the antibodies may be contained within hybridoma supernatant or ascites and utilized either directly as such or following concentration using standard techniques. In other applications, the antibodies may be further purified using, for example, salt fractionation and ion exchange chromatography, or affinity chromatography using Protein A, Protein G, Protein A/G, and/or Protein L ligands covalently coupled to a solid support such as agarose beads, or combinations of these techniques. The antibodies may be stored in any suitable format, including as a frozen preparation (e.g., −20° C. or −70° C.), in lyophilized form, or under normal refrigeration conditions (e.g., 4° C.). When stored in liquid form, a suitable buffer such as Tris-buffered saline (TBS) or phosphate buffered saline (PBS) may be utilized.

The binding agents described herein are not in any way limited to antibodies. The binding agents may be any compound exhibiting similar binding properties as antibodies (e.g., a mimetic). For example, an exemplary binding agent may be one that binds SEQ ID NO.: 1 and/or SEQ ID NO.: 2 (or a polypeptide comprising SEQ ID NO.: 1 and/or 2) and/or can compete with a monoclonal antibody binding thereto (e.g., monoclonal antibodies 1E4, 1G10, and/or 1G1). In some embodiments, the binding agent may exhibit substantially the same $K_d$ in binding assays as the binding agent (e.g., monoclonal antibody) to which it is being compared. For instance, the $K_d$ of a particular binding agent may be measured by any suitable assay including but not limited to the FACS assay described in the Examples (e.g., FIG. 1). One binding agent may be said to have "substantially the same $K_d$" as another where the measurements are within about any of 1-20, 1-5, 5-10, 10-15, or 15-20 percent of one another.

Exemplary mimetics may include, for example, organic compounds that specifically bind canine CD20 (e.g., SEQ ID NO.: 1, 2, and/or 59, and/or polypeptides comprising any such sequences) (see, e.g., Gebauer et al., *Curr. Opin. Chem. Biol.* 13 (3):245-255, 2009). Such mimetics may be, for example, an affibody (Nygren, et al., *FEBS J.* 275(11):2668-76, 2008), affilin (Ebersbach, et al., *J. Mol. Biol.* 372 (1):172-85, 2007), affitin (Krehenbrink et al., *J. Mol. Biol.* 383(5):1058-68, 2008), anticalin (Skerra, A., *FEBS J.* 275 (11):2677-83, 2008), avimer (Silverman et al., *Nat. Biotechnol.* 23(12): 1556-61, 2005), DARPin (Stumpp et al., *Drug Discov. Today* 13(15-16):695-701, 2008), Fynomer (Grabulovski et al., *J. Biol. Chem.* 282(5):3196-3204.2007), Kunitz domain peptide (Nixon et al., *Curr. Opin. Drug Discov. Devel.* 9(2):261-8, 2006), and/or a monobody (Koide et al., *Methods Mol. Biol.* 352:95-109, 2007). Other mimetics may also include, for example, derivative of an antibody (of, for example, the monoclonal antibody 1E4, 1G10, and/or 1G1) such as, for example, an Fab, F(ab')$_2$, Fab' single chain antibody, Fv, single domain antibody, mono-specific antibody, bi-specific antibody, tri-specific antibody, multi-valent antibody, chimeric antibody, canine-human chimeric antibody, canine-mouse chimeric antibody, antibody comprising a canine Fc, humanized antibody, human antibody, caninized, CDR-grafted antibody, shark antibody, nanobody (e.g., antibody consisting of a single monomeric variable domain), camelid antibody (e.g., antibodies of members of the Camelidae family), microbody, intrabody (e.g., intracellular antibody), and/or de-fucosylated antibody and/or derivative thereof. Other binding agents are also provided herein as would be understood by one of ordinary skill in the art.

In certain embodiments, preparations of binding agents are provided. Such preparations may comprise, for example, unpurified antibody as found in hybridoma supernatants or ascites preparation, partially purified preparations, or purified preparations. Thus, provided herein are antibody preparations containing one or more binding agents purified to about 50%, 60%, 75%, 90%, or 95% purity. Typically, such preparations include a buffer such as phosphate- or tris-buffered saline (PBS or TBS, respectively). The preparations may also be formulated to contain excipients, like stabilizers, for example. The preparations may also, or alternatively, comprise derivatives of such binding agents such as, for example, Fab, F(ab')₂ or single chain antibodies (Fv for example), caninized antibodies, chimeric antibodies, canine antibodies, and the like. Where the binding agents are antibodies, nucleotide sequences encoding the variable regions thereof may also be isolated from the hybridomas expressing the same cloned into expression vectors to produce certain antibody preparations (e.g., caninized antibodies). Methods for producing such preparations are well-known in the art.

The skilled artisan has many suitable techniques for using the binding agents (e.g., antibodies) described herein to identify biological samples containing proteins that bind thereto. For instance, antibodies may be utilized to isolate canine CD20 protein using, for example, immunoprecipitation or other capture-type assay. This well-known technique is performed by attaching the antibody to a solid support or chromatographic material (e.g., a bead coated with Protein A, Protein G and/or Protein L). The bound antibody is then introduced into a solution either containing or believed to contain the CD20 protein (e.g., a canine B cell lysate). Canine CD20 protein may then bind to the antibody and non-binding materials are washed away under conditions in which the CD20 protein remains bound to the antibody. The bound protein may then be separated from the antibody and analyzed as desired. Similar methods for isolating a protein using an antibody are well-known in the art. The binding agents (e.g., antibodies) may also be utilized to detect CD20 protein within a biological sample. For instance, the antibodies may be used in assays such as, for example, flow cytometric analysis, ELISA, immunoblotting (e.g., western blot), in situ detection, immunocytochemistry, and/or immunohistochemistry. Methods of carrying out such assays are well-known in the art.

To assist the skilled artisan in using the antibodies described herein, the same may be provided in kit format. A kit including such antibodies and optionally other components necessary for using the antibodies to detect cells expressing canine CD20 is provided. The antibodies of the kit may be provided in any suitable form, including frozen, lyophilized, or in a pharmaceutically acceptable buffer such as TBS or PBS. The kit may also include other reagents required for utilization of the antibodies in vitro or in vivo such as buffers (e.g., TBS, PBS), blocking agents (solutions including nonfat dry milk, normal sera, Tween-20 Detergent, BSA, or casein), and/or detection reagents (e.g., goat anti-mouse IgG biotin, streptavidin-HRP conjugates, allophycocyanin, B-phycoerythrin, R-phycoerythrin, peroxidase, detectable labels (e.g., fluoresceins, like DyLight, Cy3, Cy5, FITC, HiLyte Fluor 555, HiLyte Fluor 647; 5-carboxy-2,7-dichlorofluorescein, 5-Carboxyfluorescein (5-FAM), S-HAT (Hydroxy Tryptamine), 5-Hydroxy Tryptamine (HAT), 6-JOE; 6-carboxyfluorescein (6-FAM). FITC, 6-carboxy-1,4-dichloro-2',7'-dichlorofluorescein (TET), 6-carboxy-1,4-dichloro-2',4',5',7'-tetra-chlorofluorescein (HEX), 6-carboxy-4',5'-dichloro-2',7'-dimethoxyfluorescein (JOE); Alexa fluors, like 350, 405, 430, 488, 500, 514, 532, 546, 555, 568, 594, 610, 633, 635, 647, 660, 680, 700, 750; BODIPY fluorophores, like 492/515, 493/503, 500/510, 505/515, 530/550, 542/563, 558/568, 564/570, 576/589, 581/591, 630/650-X, 650/665-X, 665/676, FL, FL ATP, Fl-Ceramide, R6G SE, TMR, TMR-X conjugate, TMR-X, SE, TR, TR ATP, TR-X SE; Rhodamines, like 110, 123, B, B 200, BB, BG, B extra, 5-carboxytetramethylrhodamine (5-TAMRA), 5 GLD, 6-Carboxyrhodamine 6G, Lissamine, Lissamine Rhodamine B, Phallicidine, Phalloidine, Red, Rhod-2, ROX (6-carboxy-X-rhodamine), 5-ROX (carboxy-X-rhodamine), Sulphorhodamine B can C, Sulphorhodamine G Extra, TAMRA (6-carboxytetramethylrhodamine), Tetramethylrhodamine (TRITC), WT, Texas Red, Texas Red-X) and other labels and/or staining kits (e.g., ABC Staining Kit, Pierce). The kits may also include other reagents and/or instructions for using the antibodies in commonly utilized assays described above such as, for example, flow cytometric analysis, ELISA, immunoblotting (e.g., western blot), in situ detection, immunocytochemistry, immunohistochemistry. In one embodiment, the detectable labels may be fixably attached to the binding agents. In one example, the detectable labels are fixably attached to the binding agents by chemical bonds. In one example, the chemical bonds are covalent chemical bonds. In one example, the detectable labels are conjugated to the binding agents.

In one embodiment, the kit provides a monoclonal antibody in purified form. In another embodiment, the monoclonal antibody may be provided in biotinylated form either alone or along with an avidin-conjugated detection reagent (e.g., antibody). In another embodiment, the kit includes fluorescently-labelled antibodies that may be used to directly detect canine CD20. Buffers and the like required for using any of these systems are well-known in the art and may be prepared by the end-user or provided as a component of the kit. The kit may also include a solid support containing positive- and negative-control protein and/or tissue samples. For example, kits for performing spotting or western blot-type assays may include control cell or tissue lysates for use in SDS-PAGE or nylon or other membranes containing pre-fixed control samples with additional space for experimental samples. Kits for visualization of canine CD20 in cells on slides may include pre-formatted slides containing control cell or tissue samples with additional space for experimental samples.

The binding agents described herein and/or derivatives thereof may also be incorporated into compositions for use in vitro or in vivo. The antibodies or derivatives thereof may also be fixably attached to functional/effector moieties such as cytotoxic drugs or toxins, or active fragments thereof such as diphtheria A chain, exotoxin A chain, ricin A chain, abrin A chain, curcin, crotin, phenomycin, enomycin, among others. Functional moieties may also include radiochemicals. In one embodiment, the effector moieties may be fixably attached to the binding agents. In one example, the detectable labels are fixably attached to the binding agents by chemical bonds. In one example, the chemical bonds are covalent chemical bonds. In one example, the effector moieties are conjugated to the binding agents.

The binding agents may be used alone or in combination with another agent for preventing and/or treating disease. One such disease is B cell lymphoma (e.g., diffuse large cell B cell lymphoma, follicular lymphoma, mucosa-associated lymphatic tissue lymphoma (MALT), small cell lymphocytic lymphoma, chronic lymphocytic leukemia, mantel cell lymphoma, Burkitt's lymphoma, mediastinal large B cell lymphoma, Waldenstrom macroglobulinemia, nodal marginal zone B cell lymphoma (NMZL), splenic marginal zone lymphoma (SMZL), intravascular large B-cell lymphoma, primary effusion lymphoma, lymphomatoid granulomatosis, and the like), particularly in canine animals. The binding agents may also be combined with or used in conjunction with (e.g., as part of a treatment regimen) other anti-cancer agents such as, for example, cyclophosphamide (e.g., Cytoxan, Neosar). Adriamycin (e.g. doxorubicin/hydroxy-doxorubicin), vincristine (e.g., Oncovin), prednisone (e.g., Deltasone, Orasone). L-asparaginase, chlorambucil, lomustine (CCNU), cytosine arabinoside, mitoxantrone, and for combinations thereof. A combination of such anti-cancer agents may refer to simultaneous and/or sequential administration.

The binding agents may also be used treat various autoimmune diseases. Example diseases may include, but are not limited to, autoimmune hemolytic anemia, immune-mediated thrombocytopenia, lupus, autoimmune blistering diseases, immune-mediated arthritis and atopic dermatitis.

The antibodies described herein and/or derivatives thereof may be used in assays to determine the presence of a disease state in a patient, to predict prognosis, or to determine the effectiveness of a chemotherapeutic or other treatment regimen. Expression profile assays, performed as described herein or as is otherwise known in the art, may be used to determine the relative level of expression of CD20. The level of expression may then be correlated with base (e.g., control) levels to determine whether a particular disease is present within the patient, the patient's prognosis, or whether a particular treatment regimen is effective. For example, if the patient is being treated with a particular chemotherapeutic regimen, a decreased level of expression of an immunogenic target in the patient's tissues (e.g., in peripheral blood, breast tissue biopsy) may indicate the regimen is decreasing the cancer load in that host. Similarly, if the level of expression is increasing, this may indicate the regimen is not having the desired effect and another therapeutic modality may be selected.

It is also possible to use the antibodies described herein as reagents in drug screening assays. The reagents may be used to ascertain the effect of a drug candidate on the expression of the immunogenic target in a cell line, or a cell or tissue of a patient. The expression profiling technique may be combined with high throughput screening techniques to allow rapid identification of useful compounds and monitor the effectiveness of treatment with a drug candidate (see, for example, Zlokarnik et al., *Science* 279:84-8, 1998). Drug candidates may be chemical compounds, nucleic acids, proteins, antibodies, or derivatives therefrom, whether naturally occurring or synthetically derived. Drug candidates thus identified may be utilized, among other uses, as pharmaceutical compositions for administration to patients or for use in further screening assays.

The antibodies described herein may be prepared as an injectable preparation, such as in suspension in a non-toxic parenterally acceptable diluent or solvent. Suitable vehicles and solvents that may be utilized include water, Ringer's solution, and isotonic sodium chloride solution, TBS and PBS, among others. The formulations may contain excipients, like stabilizers, for example. In certain applications, the antibodies are suitable for use in vitro. In other applications, the antibodies are suitable for use in viva. The preparations suitable for use in either case are well-known in the art and will vary depending on the particular application.

Preparation of Binding Agents and Immunization

Also provided herein are canine CD20 polypeptides and/or fragments and/or derivatives thereof (collectively referred to herein as "canine CD20"), as well as methods of preparing and using the same. An exemplary canine CD20 may comprise the amino acid sequence shown below:

(SEQ ID NO.: 59)
NITISHFKMENLNLIKAPMPYVDIHNCDPANPSEKNSLSIQYCGSI.

Exemplary fragments of SEQ ID NO.: 59 may be SEQ ID NOS. 1 and/or 2. Thus, an exemplary canine CD20 may comprise SEQ ID NO. 59, SEQ ID NO.: 1, and/or SEQ ID NO.: 2.

Canine CD20 typically exhibits the ability to induce anti-CD20 antibodies in a host. Host animals generally are mammals, including but not limited to a mouse, dog, cat, goat, sheep, human being, and the like. In one example, the host may be a mouse. Administration of the canine CD20 (for example, SEQ ID NOS. 1, 2 and/or 59) results in production of anti-canine CD20 antibodies in the mouse. In one example, the host may be a dog and administration of the canine CD20 may result in production of an immune response in the dog that may be specific for cells expressing CD20. The antibodies may be non-protective and/or non-neutralizing, and/or may be protective and/or neutralizing antibodies, following administration to the host animal.

In certain embodiments, the antibodies may be used to detect and/or isolate canine CD20 and/or to detect, isolate, and/or destroy cells expressing canine CD20. In certain embodiments, the canine CD20 may share amino acid sequence identity (e.g., any of about 90%, 95%, 98%, 99%, or 99.9%) with other CD20 polypeptides (e.g., canine or otherwise). Any differences in the amino acid sequence between CD20 polypeptides are typically but not necessarily phenotypically silent, but should be useful for generating anti-CD20 immunity (e.g., inducing the production of anti-CD20 antibodies in a host).

Nucleic acids encoding CD20 are also provided, along with variants of such sequences (e.g., degenerate variants thereof). In certain embodiments, a nucleic acid molecule encoding canine CD20 may be inserted into one or more expression vectors, as discussed below in greater detail. In such embodiments, canine CD20 may be encoded by nucleotides corresponding to the amino acid sequence. The particular combinations of nucleotides that encode the various amino acids are well known in the art, as described in various references used by those skilled in the art (e.g., Lewin, B., Genes V, Oxford University Press, 1994). The nucleotide sequences encoding canine CD20 may be ascertained with reference to Table 6, for example. Nucleic acid variants may use any combination of nucleotides that encode the polypeptide of interest.

TABLE 6

| Phe (F) | TTT<br>TTC | Ser<br>(S) | TCT<br>TCC | Tyr (Y) | TAT<br>TAC | Cys (C) | TGT<br>TGC |
|---|---|---|---|---|---|---|---|
| Leu (L) | TTA<br>TTG<br>CTT<br>CTC<br>CTA<br>CTG | Pro<br>(P) | TCA<br>TCG<br>CCT<br>CCC<br>CCA<br>CCG | TERM<br>His (H)<br>Gln (Q) | TAA<br>TAG<br>CAT<br>CAC<br>CAA<br>CAG | TERM<br>Trp (W)<br>Arg (R) | TGA<br>TGG<br>CGT<br>CGC<br>CGA<br>CGG |
| Ile (I) | ATT<br>ATC<br>ATA | Thr<br>(T) | ACT<br>ACC<br>ACA | Asn (N)<br>Lys (K) | AAT<br>AAC<br>AAA | Ser (S)<br>Arg (R) | AGT<br>AGC<br>AGA |
| Met (M) | ATG | | ACG | | AAG | | AGG |
| Val (V) | GTT<br>GTC<br>GTA<br>GTG | Ala<br>(A) | GCT<br>GCC<br>GCA<br>GGG | Asp (D)<br>Glu (E) | GAT<br>GAC<br>GAA<br>GAG | Gly (G) | GGT<br>GGC<br>GGA<br>GGG |

Modified CD20 may comprise at least one amino acid substitution, insertion, and/or deletion. Modified CD20 will typically remain substantially non-toxic and/or elicit neutralizing antibodies upon administration to a host. Such antibodies may bind to the same epitope as antibodies elicited following administration of another CD20 to a host. As described herein, canine CD20 may be useful in immunogenic compositions or vaccines for prevention and/or treatment of conditions for which targeting cells expressing CD20 would be beneficial (e.g., cancer such as B cell lymphoma). Suitable modifications may introduce conservative changes in the amino acid sequence of canine CD20. Conservative amino acid substitutions may involve a substitution of a native amino acid residue with a non-native residue such that there is little or no effect on the size, polarity, charge, hydrophobicity, or hydrophilicity of the amino acid residue at that position and, in particular, does not result in decreased immunogenicity. Suitable conservative amino acid substitutions are shown in Table 7.

TABLE 7

| Original Residues | Exemplary Conservative Substitutions | Preferred Conservative Substitution |
|---|---|---|
| Ala | Val, Leu, Ile | Val |
| Arg | Lys, Gln, Asn | Lys |
| Asn | Gln | Gln |
| Asp | Glu | Glu |
| Cys | Ser, Ala | Ser |
| Gln | Asn | Asn |
| Glu | Asp | Asp |
| Gly | Pro, Ala | Ala |
| His | Asn, Gln, Lys, Arg | Arg |
| Ile | Leu, Val, Met, Ala, Phe, Norleucine | Leu |
| Leu | Norleucine, Ile, Val, Met, Ala, Phe | Ile |
| Lys | Arg, 1,4 Diamino-butyric Acid, Gln, Asn | Arg |
| Met | Leu, Phe, Ile | Leu |
| Phe | Leu, Val, Ile, Ala, Tyr | Leu |
| Pro | Ala | Gly |
| Ser | Thr, Ala, Cys | Thr |
| Thr | Ser | Ser |
| Trp | Tyr, Phe | Tyr |
| Tyr | Trp, Phe, Thr, Ser | Phe |
| Val | Ile, Met, Leu, Phe, Ala, Norleucine | Leu |

The specific amino acid substitution selected may depend on the location of the site selected.

The anti-CD20 antibodies, may be combined with one or more pharmaceutically acceptable carriers prior to administration to a host. A pharmaceutically acceptable carrier is a material that is not biologically or otherwise undesirable, e.g., the material may be administered to a subject, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

Suitable pharmaceutical carriers and their formulations are described in, for example, *Remington's: The Science and Practice of Pharmacy, 21st Edition*, David B. Troy, ed., Lippincott Williams & Wilkins (2005). Typically, an appropriate amount of a pharmaceutically-acceptable salt is used in the formulation to render the formulation isotonic. Examples of the pharmaceutically-acceptable carriers include, but are not limited to, sterile water, saline, buffered solutions like Ringer's solution, and dextrose solution. The pH of the solution is generally from about 5 to about 8 or from about 7 to about 7.5. Other carriers include sustained-release preparations such as semipermeable matrices of solid hydrophobic polymers containing polypeptides or fragments thereof. Matrices may be in the form of shaped articles, e.g., films, liposomes or microparticles. It will be apparent to those persons skilled in the art that certain carriers may be more preferable depending upon, for instance, the mute of administration and concentration of composition being administered. Carriers are those suitable for administration of polypeptides and/or fragments thereof to humans or other subjects.

Pharmaceutical compositions may also include carriers, thickeners, diluents, buffers, preservatives, surface active agents, adjuvants, immunostimulants, in addition to the immunogenic polypeptide, or the anti-CD20 antibodies. Pharmaceutical compositions may also include one or more active ingredients such as antimicrobial agents, antiinflammatory agents and anesthetics The compositions described herein may be administered to animals in vivo to generate an immune response against an immunogen (e.g., SEQ ID NOS. 1, 2 and/or 59), to detect cells expressing canine CD20, and/or treat a disease condition in which cells expressing CD20 may need to be eliminated (e.g., B cell lymphoma). In certain embodiments, this disclosure also provides binding agents such as antibodies (e.g., including monoclonal antibodies) useful in the isolation and/or identification of cells expressing canine CD20 or a cell surface protein that reacts with such binding agents (e.g., B cells, B lymphoma cells, canine CD20) and/or treatment and prevention of cancer in a mammal (e.g., a canine). Thus, in certain embodiments, the binding agent may be an antibody reactive against canine CD20 expressed on the cell surface. In some embodiments, the one or more binding agents (e.g., an antibody such as a monoclonal antibody) that binds to or reacts with canine CD20 at a region thereof which comprises SEQ ID NO.: 1, SEQ ID NO.: 2, and/or SEQ ID NO.: 59 (and/or fragments and/or derivatives thereof).

Uses of Binding Agents

In some embodiments, methods for detecting canine cells using binding agents are provided. In certain embodiments, cells expressing CD20 on their cell surface (e.g., B cell lymphoma) in an animal (e.g., a canine), can be detected by contacting a test biological sample with a binding agent or derivative thereof and detecting the binding agent bound to the biological sample or components thereof. In certain embodiments, the method may comprise comparing the amount of binding to the test biological sample or components thereof to the amount of binding to a control biological sample or components thereof, wherein increased binding to the test biological sample or components thereof relative to the control biological sample or components thereof indicates the presence of a lymphoma cell in the test biological sample. In some embodiments, the biological sample may be canine blood or needle aspirates. Such methods are also provided in an in vivo and/or in vitro format.

In some embodiments, methods for decreasing the viability and/or number of cells expressing canine CD20 in a host using such binding agents are also provided. Methods for treating one or more disease conditions (e.g., lymphoma) in a mammalian host comprising administering to the mammal at least one or more effective doses of one or more binding agents (and/or derivative(s) thereof) described herein are also provided. In some embodiments, the binding agent is a monoclonal antibody or fragment or derivative thereof comprising one or more of the amino acid sequences shown in Tables 1, 4, and/or 5. The binding agent may be administered in a dosage amount of about 1 to about 50 mg/kg of body weight of the mammal, about 1 to about 30 mg/kg, or about 1 to about 15 mg/kg (e.g., about any of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, or 40 mg/kg). In certain embodiments, the binding agent may be administered to the mammal (e.g., intradermally, intravenously, orally, rectally) at about 1, 5 or 10 mg/kg one or more times. When multiple doses are administered, the doses may comprise about the same or different amounts of binding agent in each dose. The doses may also be separated in time from one another by the same or different intervals. For instance, the doses may be separated by about any of 6, 12, 24, 36, 48, 60, 72, 84, or 96 hours, one week, two weeks, three weeks, one month, two months, three months, four months, five months, six months, seven months, eight months, nine months, 10 months, 11 months, 12 months, 1.5 years, 2 years, 3 years, 4 years, 5 years, or any time period before, after, and/or between any of these time periods. In some embodiments, the binding agents may be administered in conjunction with other agents (e.g., chemotherapeutic agents), as described above. Such other agents may be administered about simultaneously with the binding agents, or at a different time and/or frequency. Other embodiments of such methods may also be appropriate as could be readily determined by one of ordinary skill in the art.

Generally, a dose of the monoclonal antibody that has the effect of decreasing the number, proliferation, detrimental effects, and so on, of the cancer cells in a dog, is called an effective dose.

Kits comprising any of the immunogens and/or binding agents described herein, optionally also including instructions for using such immunogens and/or binding agents, are also provided, and may facilitate the methods. For example, a kit may contain a composition comprising a binding agent (e.g., mouse monoclonal antibody or chimeric antibody preparation). The composition may further comprise a pharmaceutically acceptable carrier (e.g., phosphate-buffered saline) and may be in solution, frozen, lyophilized, or other suitable form. The kit may also include one or more control binding agents (e.g., a negative control that does not bind the target of the assay for which the kit is designed, or a positive control which may be supplied along with a sample to which the positive control is known to bind) and/or instructions for use. As the kits could be used for in vitro or in vivo assays and/or treatments (e.g., a kit for administration to a mammal), the instructions may vary depending on the particular use for which the kit is designed. Other embodiments of such kits that could be provided would be readily apparent to one of ordinary skill in the art.

It must be noted that, as used in the specification and the appended claims, the singular forms "a". "an", and "the" include plural referents unless the context clearly dictates otherwise. Thus, for example, reference to a fragment may include mixtures of fragments and reference to a pharmaceutical carrier or adjuvant may include mixtures of two or more such carriers or adjuvants.

The terms "about", "approximately", and the like, when preceding a list of numerical values or range, refer to each individual value in the list or range independently as if each individual value in the list or range was immediately preceded by that term. The terms mean that the values to which the same refer are exactly, close to, or similar thereto.

As used herein, a subject or a host is meant to be an individual. The subject or host may include domesticated animals, such as cats and dogs, livestock (e.g., cattle, horses, pigs, sheep, and goats), laboratory animals (e.g., mice, rabbits, rats, guinea pigs) birds, and/or human beings, for example. In some embodiments, the subject or host may be a mammal such as a canine animal.

Optional or optionally means that the subsequently described event or circumstance can or cannot occur, and that the description includes instances where the event or circumstance occurs and instances where it does not. For example, the phrase optionally the composition can comprise a combination means that the composition may comprise a combination of different molecules or may not include a combination such that the description includes both the combination and the absence of the combination (e.g., individual members of the combination).

Ranges may be expressed herein as from about one particular value, and/or to about another particular value. When such a range is expressed, another aspect includes from the one particular value and/or to the other particular value. Similarly, when values are expressed as approximations, by use of the antecedent about or approximately, it will be understood that the particular value forms another aspect. It will be further understood that the endpoints of each of the ranges are significant both in relation to the other endpoint, and independently of the other endpoint. Ranges (e.g., 90-100%) are meant to include the range per se as well as each independent value within the range as if each value was individually listed.

When the terms prevent, preventing, and prevention are used herein in connection with a given treatment for a given condition (e.g., preventing infection by *Streptococcus* sp.), it is meant to convey that the treated patient either does not develop a clinically observable level of the condition at all, or develops it more slowly and/or to a lesser degree than he/she would have absent the treatment. These terms are not limited solely to a situation in which the patient experiences no aspect of the condition whatsoever. For example, a treatment will be said to have prevented the condition if it is given during exposure of a patient to a stimulus that would have been expected to produce a given manifestation of the condition, and results in the patient's experiencing fewer and/or milder symptoms of the condition than otherwise expected.

All references cited within this disclosure are hereby incorporated by reference in their entirety. Certain embodiments are further described in the following examples. These embodiments are provided as examples only and are not intended to limit the scope of the claims in any way. All references cited herein are hereby incorporated by reference. A better understanding of the present invention and of its many advantages will be had from the following examples, given by way of illustration.

EXAMPLES

Example 1 mAbs Reactive Against Canine CD20

A. Generation and Selection of Hybridomas

To generate mouse monoclonal antibodies against canine CD20, the $2^{nd}$ extracellular domain (ECD) of canine CD20 was cloned from canine PBMC cDNA, expressed as a mouse $F_c$ fusion protein ("ECD2-mFc"), and used as the immunogen. Canine ECD2-mFC has the amino acid sequences of SEQ ID NOS. 59 and 60, as shown below:

```
                                            (SEQ ID NO. 59)
NITISHFFKMENLNLIKAPMPYVDIHNCDPANPSEKNSLSIQYCGSI;
and, (SEQ ID NO.: 60)
RSLEVLFQGPGSPPLKECPPCAAPDLLGGPSVFIFPPPKIKDVLMISLS

PMVTCVVVDVSEDDPDVQISWFVNNVEVHTAQTQTHREDYNSTLRVVS
```

-continued

ALPIQHQDWMSGKEFKCKVNNRALPSPIEKTISKPRGPVRAPQVYVLP

PPAEEMTKKEFSLTCMITGFLPAEIAVDWTSNGRETQNYKNTATVLDS

DGSYFMYSKLRVQKSTWERGSLFACSVVHEGLHNHLTTKTISRSLGK.

The immunogen contained a linear arrangement of SEQ ID NO.: 59 and SEQ ID NO. 60 and is set forth as SEQ ID NO.: 61:

(SEQ ID NO.: 61)
NITISHFFKMENLNLIKAPMPYVDIHNCDPANPSEKNSLSIQYCGSI

RSLEVLFQGPGSPPLKECPPCAAPDLLGGPSVFIFPPKIKDVLMISLSP

MVTCVVVDVSEDDPDVQISWFVNNVEVHTAQTQTHREDYNSTLRVVSAL

PIQHQDWMSGKEFKCKVNNRALPSPIEKTISKPRGPVRAPQVYVLPPPA

EEMTKKEFSLTCMITGFLPAEIAVDWTSNGRETQNYKNTATVLDSDGSY

FMYSKLRVQKSTWERGSLFACSVVHEGLHNHLTTKTISRSLGK.

Hybridomas were generated following immunization of mice with the SEQ ID NO.: 59/SEQ ID NO.: 60 fusion protein (SEQ ID NO.: 61). A primary ELISA screen was carried out using ECD2-hFc fusion protein as the antigen. Positive hybridomas were then subjected to a secondary screen using a mixture of fresh (CD20$^+$) and cultured (CD20$^-$) canine B-cell lymphoma cells. Clones that displayed bifurcated FACS profiles were selected for further screening. Three mAbs expressed from hybridomas generated in this approach (1E4, 1G1, and 1G10) were selected for further characterization.

The relative affinities of the mouse monoclonal antibodies 1E4, 1G1, and 1G10 for binding to canine CD20 was determined by fluorescent activated cell sorting (FACS) using canine B cell lymphoma cells, which express canine CD20. The mAbs 1E4 and 1G10 were found to exhibit the highest relative affinity to CD20: 1G10 ($K_d$=0.29 nm)>1E4 ($K_d$=0.97 nm)>>1G1 ($K_d$=19.78 nm)) (FIG. 1).

Figure 2:
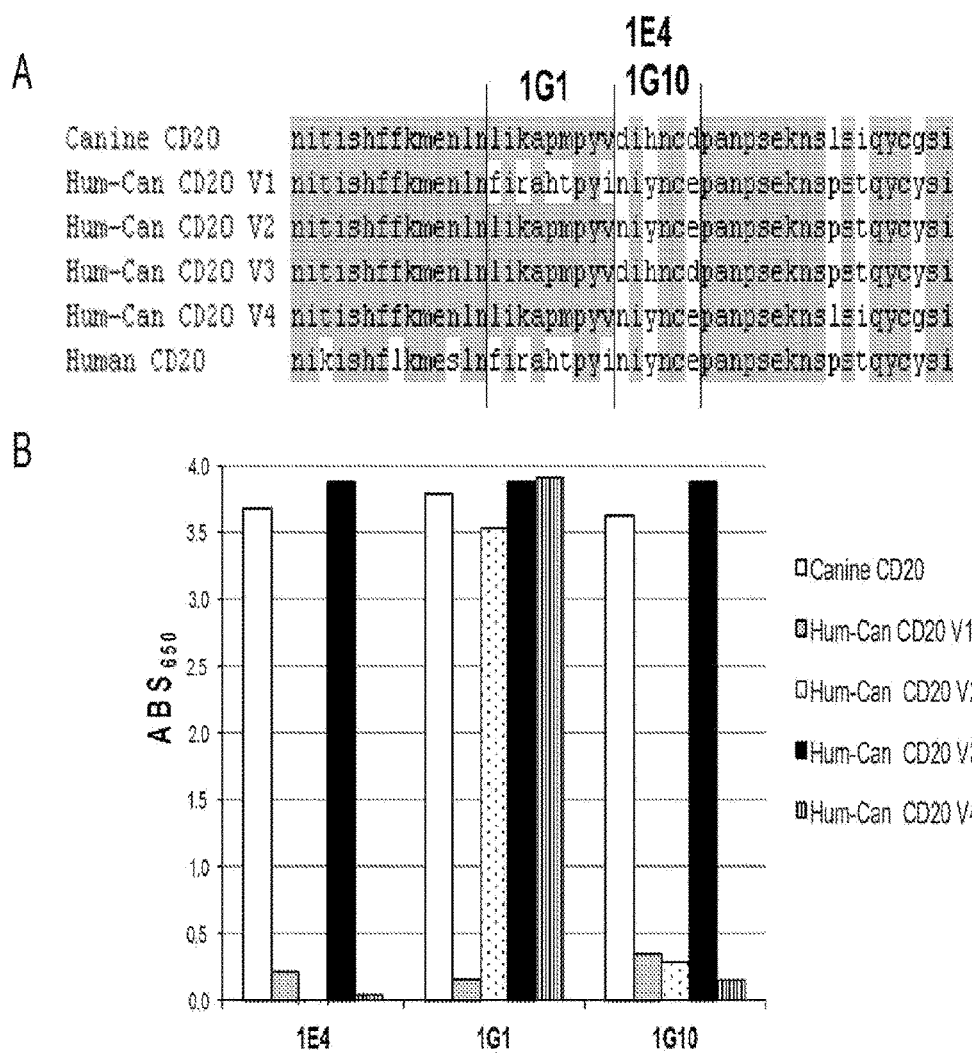
FIG. 2. A. Alignment of canine and human extracellular domains of CD20 and human/canine hybrid variants V1-V4. B. ELSA binding analysis of hybridoma antibodies 1E4, 1G1, and 1G10 to canine CD20 ECD2 and V1-V4.

In order to identify the epitope on canine CD20 that was bound by the mouse monoclonal antibodies 1E4, 1G1, and 1G10 (none of which bind human CD20), several expression constructs encoding hybrid versions of the original immunogen (cCD20 ECD2-mFc) were generated (FIG. 2A). The amino acid sequences of the hybrid CD20 polypeptides are also shown below:

As illustrated in FIG. 2A, the hybrid proteins expressed from these vectors contained human CD20 sequences interspersed into canine CD20 in different portions of extracellular domain 2. This strategy enabled identification of the specific sequences in canine CD20 that each mAb binds. Binding was tested using a standard ELISA protocol. Briefly, recombinant canine CD20 ECD2-mFc fusion protein and human/canine hybrid variants thereof were diluted in PBS and bound to a 96-well microtiter plate at 200 ng/well by overnight incubation at 4° C. The plate was rinsed three times with PBST buffer, blocked with a solution of 3% BSA in PBS for one hour at 37° C., then rinsed once with PBST. Mouse monoclonal antibodies 1E4, 1G1, and 1G10 were diluted to a concentration of 5 μg/ml in PBS and 50 μl of this dilution was applied to the plate for 1 hour at room temperature. The plate was then rinsed three times with PBST, and Jackson Immunoresearch goat anti-mouse-IgG light chain-specific HRP conjugate (#115-035-174) diluted to 1:5000 in PBS (50 μL) was added to each well, and the plate was incubated for 45 min at room temperature. The plate was washed three times with PBST, then 100 μL of SureBlueTMB substrate (KPL #52-00-03) was added to each well and the plate was incubated for about 10 min at room temperature. The plate was read at 650 nm in a spectrophotometer.

The data presented in FIG. 2B demonstrate that mAbs 1E4 and 1G10 bound better to hybrid versions of cCD20 ECD2-mFc that contained the canine CD20 epitope DIHNCD (SEQ ID NO.: 2) in the ELISA assay, indicating that these mAbs bind a region of canine CD20 that contains the amino acid sequence DIHNCD (SEQ ID NO.: 2). The mAb 1G1 bound better to CD20 proteins that contained the canine CD20 epitope LIKAPMPYV (SEQ ID NO.: 1) in the ELISA assay, indicating that 1G1 binds to a region of canine CD20 that contains the amino acid sequence LIKAPMPYV (SEQ ID NO.: 1).

Figure 3:
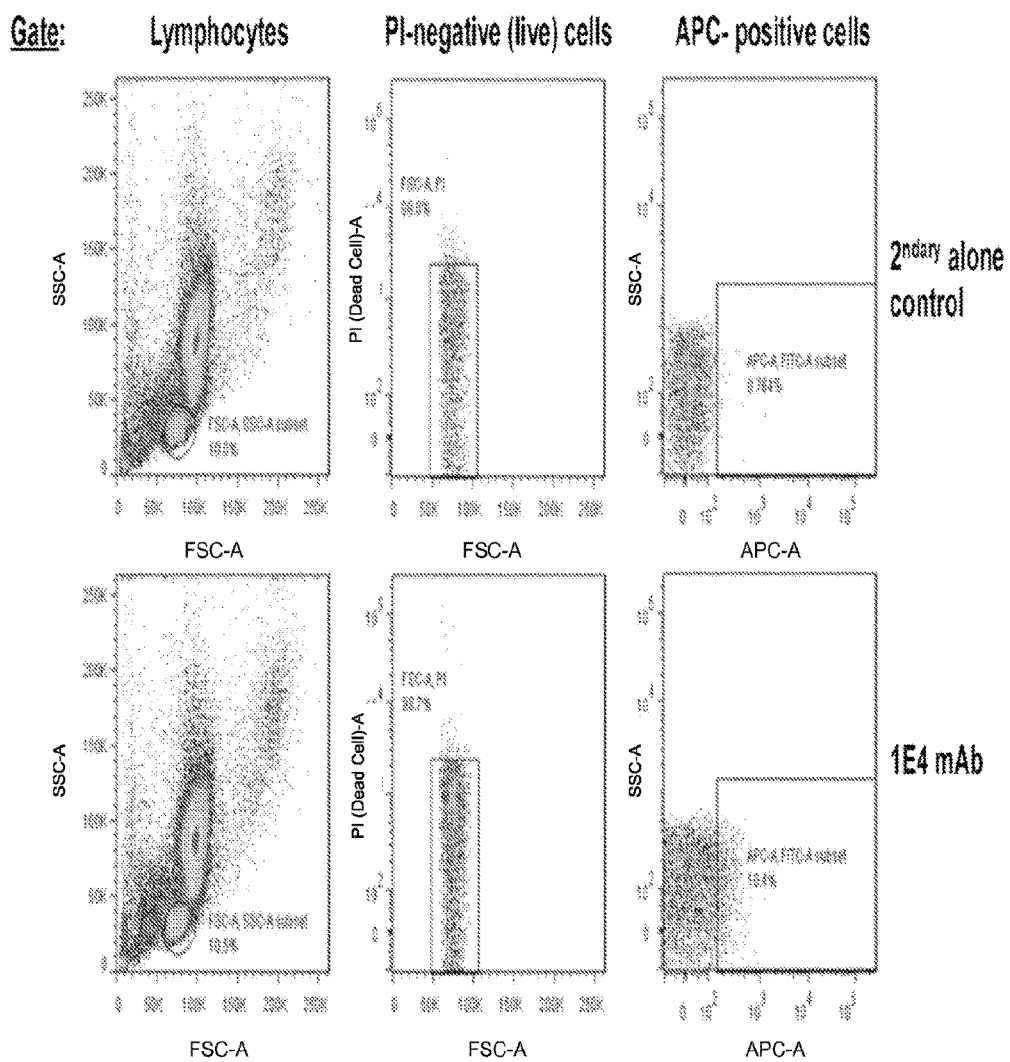
FIG. 3. FACS analysis of binding of hybridoma antibody 1E4 to canine peripheral blood mononuclear cells (PBMC).

Next, FACS was performed on canine PBMCs using purified 1E4-mAb (FIG. 3). Canine PBMC were isolated by red blood cell lysis, labeled with propidium iodide, and stained with 1E4 antibody (1 μg antibody/ml) and anti-mouse Fab-APC (1/200) from Jackson Immunoresearch #115-136-146 as the secondary antibody (secondary antibody alone was used as a negative control). The primary FACS gate was on lymphocytes (left panels). Only live lymphocytes (those that did not stain with propidium iodide) were included in the analysis (middle panels). Cells positive for antibody binding were determined by setting a gate that

TABLE 7

| Hybrid | Amino Acid Sequence |
| --- | --- |
| Canine CD20 ECD2 | NITISHFFKMENLNLIKAPMPYVDIHNCDPANPSEKNSL SIQYCGSI (SEQ ID NO.: 62) |
| Hum-Can CD20 ECD2 V1 | NITISHFFKMENLNFIRAHTPYINIYNCEPANPSEKNSP STQYCGSI (SEQ ID NO.: 63) |
| Hum-Can CD20 ECD2 V2 | NITISHFFKMENLNLIKAPMPYVNIYNCEPANPSEKNSP STQYCGSI (SEQ ID NO.: 64) |
| Hum-Can CD20 ECD2 V3 | NITISHFFKMENLNLIKAPMPYVDIHNCDPANPSEKNSP STQYCGSI (SEQ ID NO.: 65) |
| Hum-Can CD20 ECD2 V4 | NITISHFFKMENLNLIKAPMPYVNIYNCEPANPSEKNSL SIQYCGSI (SEQ ID NO.: 66) |
| Human CD20 ECD2 | NITISHFLKMESLNFIRAHTPYINIYNCEPANPSEKNSP STQYCYSI (SEQ ID NO.: 67) | included fewer than 1% positives in the negative control sample (upper right panel). Approximately 10 percent of lymphocytes were stained with 1E4 in this experiment, which is consistent with 1E4 specifically binding to CD20 on the surface of canine B cells.

B. Sequencing of Variable Regions of 1E4, 1G1, and 1G10

The variable region DNAs from the murine monoclonal antibodies were amplified by RT-PCR from RNA obtained from the hybridoma cell lines using standard methods. Forward primers used to amplify heavy and light chain variable region sequences were those reported in Chardès T. et al., *FEBS Letters*. June 11; 452(3):386-94, 1999. Reverse primers used to amplify heavy and light chain variable region sequences are shown below:

```
(heavy chain constant region primer
(SEQ ID NO.: 68))
5'-GCGTCTAGAAYCTCCACACACAGGRRCCAGTGGATAGAC-3';
and (light chain constant region primer
(SEQ ID NO.: 69))
5'-GCGTCTAGAACTGGATGGTGGGAAGATGG-3',
```

The heavy and light chain variable region amplification products were then cloned into a pcDNA3.1 vector and sequenced. The amino acid and nucleotide sequences of the 1E4, 1G1, and 1G10 variable regions are shown in Table 1.

Example 2

A. Expression of Canine Chimeric Antibodies 1E4-cIgGB and Rituxan-cIgGB in CHO Cells Genes encoding chimeric light and heavy antibody chains were constructed. A codon-optimized murine nucleotide sequence encoding the light chain variable region of the 1E4 antibody (SEQ ID NO.: 5) (Table 1) was fused to a codon-optimized nucleotide sequence encoding the light chain constant region from canine (SEQ ID NO.: 56) (Table 5), to produce a fusion gene encoding the chimeric antibody light chain.

In addition, a codon-optimized murine nucleotide sequence encoding the heavy chain variable region of the 1E4 antibody (SEQ ID NO.: 8) (Table 1) was fused to a codon-optimized nucleotide sequence encoding the heavy chain constant region of canine IgGB (SEQ ID NO.: 58) (Table 5), to produce a fusion gene encoding the canine chimeric antibody heavy chain.

The chimeric light and heavy chains sequences were constructed into a single plasmid expression vector. The vector was designed to contain separate mammalian transcription units (enhancer/promoter at 5' end, poly A sequence at 3' end) to express the chimeric light and heavy chains. The 5' coding region of each transcription unit also encoded a leader/signal sequence to provide for processing and assembly of the encoded proteins, and secretion of the anti-canine CD20 antibody, called 1E4-cIgGB. The plasmid expression vector contained a separate transcription unit encoding a protein that is selectable in mammalian cells. The plasmid expression vectors are described in WO 2009/080720 (US 2011/0045536A 1) and WO 2010/022961. A separate, similar vector encoding a canine chimeric version of an anti-human CD20 antibody, called Rituxan-cIgGB, was used as a control.

Figure 4:
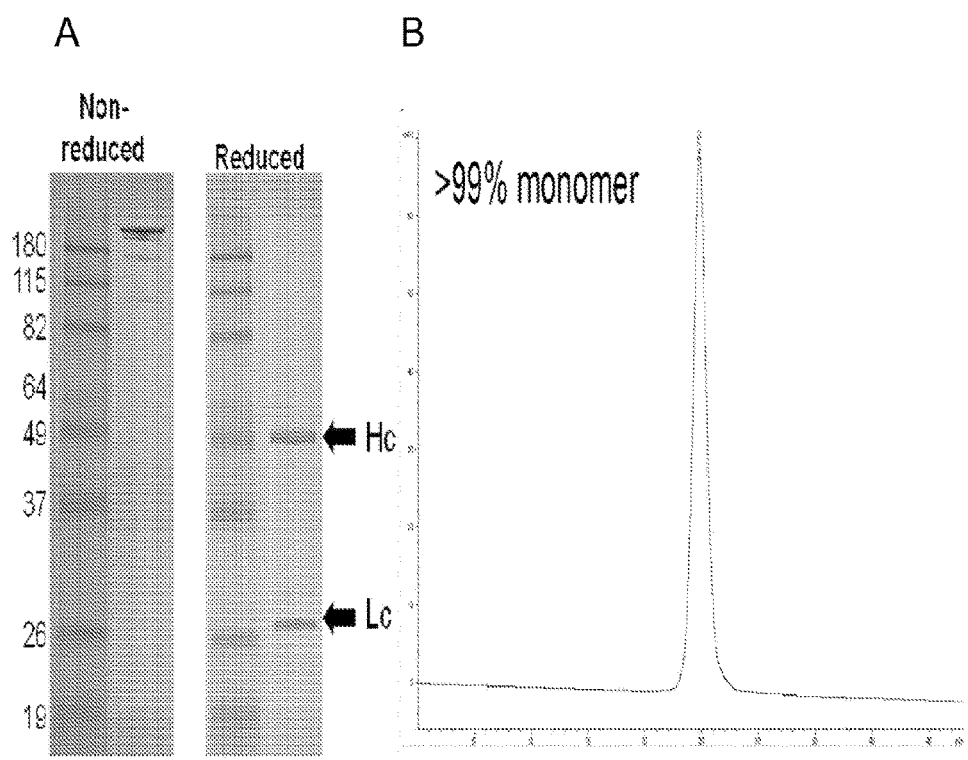
FIG. 4. A. SDS-PAGE analysis of purified chimeric anti-canine CD20 antibody 1E4-cIgGB expressed from CHO cells. B. Size exclusion chromatography analysis of purified 1E4-cIgGB.

Both the plasmids encoding 1E4-cIgGB and control Rituxan-cIgGB were transfected into CHO cells and stable pooled transfectants were selected for each as described in WO 2010/022961. Antibodies were produced from these stable antibody-expressing cell pools using standard fed-batch protocols. Antibodies secreted from these cells were purified over Protein G Sepharose columns using a GE Healthcare AKTA-FPLC liquid chromatography system. The isolated antibody preparations were analyzed by SDS-PAGE and size-exclusion chromatography (see FIG. 4 for analysis of CHO-produced 1E4-cIgGB).

B. Modification of 1E4 Light Chain

Modifications of the antibodies described were also made using the above procedures. Asparagine 33 (N33) or glycine 34 (G34) in the asparagine-glycine dipeptide sequence (Asp-Gly or N-G) of the light chain variable region ($V_L$) of 1E4 (SEQ ID NO.: 3) were modified to remove a potential deamidation site. In various embodiments, N33 was substituted by alanine (A), glutamic acid (E), phenylalanine (F), histidine (H), isoleucine (I), lysine (K), leucine (L), proline (P), glutamine (Q), arginine (R), threonine (T), valine (V), or tyrosine (Y). In some embodiments, G34 was substituted by alanine (A), glutamic acid (E), phenylalanine (F), histidine (H), isoleucine (I), lysine (K), leucine (L), proline (P), glutamine (Q), arginine (R), valine (V), or tyrosine (Y). Whole antibodies (heavy plus light chains) containing one of the above substitutions were tested by ELISA assay for their ability to bind canine CD20 ECD2 peptide (SEQ ID NO.: 62).

Figure 5:
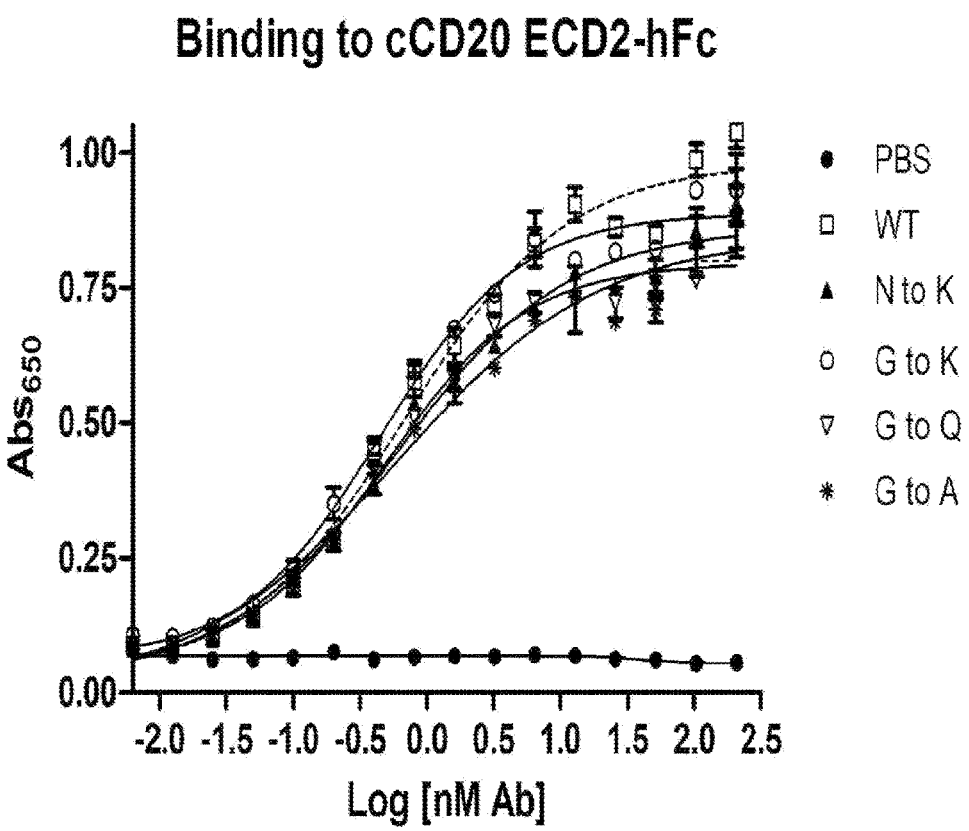
FIG. 5. ELISA analysis of binding to CD20 ECD2 peptide of increasing concentrations of unmodified (WT) 1E4-cIgGB antibody and antibodies with the indicated amino acid substitutions to the NG sequence within $V_L$ of 1E4-cIgGB.

None of the above substitutions eliminated antibody binding to ECD2 peptide and, in many cases, the effect of the substitution on antigen binding was minor. FIG. 5 illustrates the results for some of these antibodies: antibodies that contained one of substitution of N33 to K (lysine), G34 to K (lysine), G34 to Q (glutamine) or G34 to A (alanine). As shown in FIG. 5, none of these substitutions significantly affected binding to canine CD20.

Example 3

In Vivo Activity of the Chimeric Anti-Canine CD20 Antibody 1E4-cIgGB

The efficacy of the chimeric antibody 1E4-cIgGB in depleting B cells was tested in vivo in a dose-response study. It has been shown that the anti-human CD20 antibody Rituximab (Rituxan®) does not cross-react with/bind to canine CD20 (Jubala et al., *Vet Pathol.*, July; 42(4):468-76, 2005; Impellizeri et al., *Vet J.*, May; 171(3):556-8, 2006). As such, a chimeric form of Rituxan containing a canine IgGB Fc (Rituxan-cIgGB) was cloned and expressed as described above in Example 2 and used as a negative isotype control in this study. Pharmacodynamic effects were measured over 59 days of treatment with 1E4-cIgGB at multiple dose levels when administered by a single intravenous (IV) injection to naïve healthy male Beagle dogs. Pre-study body weights and pre-study clinical pathology data (clinical chemistry and hematology) were utilized to randomize dogs into their respective treatment groups. The experimental design is shown below:

TABLE 6

| Group (n = 5) | Antibody | Dose (mg/kg of animal body weight) |
| --- | --- | --- |
| 1 | Rituxan-cIgGB | 10 |
| 2 | 1E4-cIgGB | 0.1 |
| 3 | 1E4-cIgGB | 1 |
| 4 | 1E4-cIgGB | 10 |
| 5 | 1E4-cIgGB | 30 |

Figure 6:
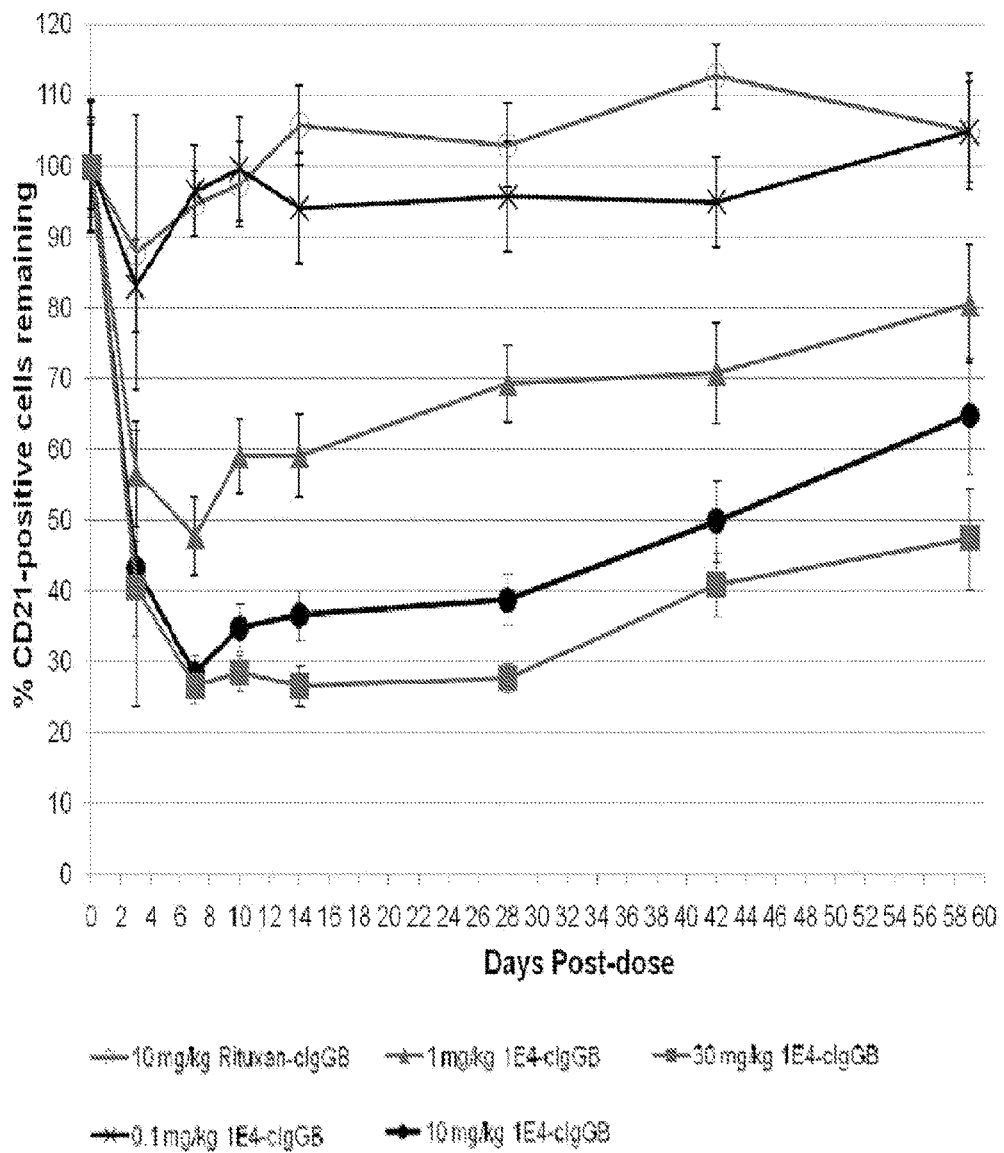
FIG. 6. Dose-dependent in vivo depletion of canine B cells using exemplary antibody 1E4-cIgGB. Rituxan-cIgGB was included as a negative (isotype) control.

On Day 1 of the study, a single dose (0.1 1, 10, or 30 mg/kg) of 1E4-cIgGB or the isotype control antibody Rituxan-cIgGB (10 mg/kg) was administered to the animals via intravenous bolus injection. Blood was collected from animals at Day 0 (pre-dose), Day 3, Day 7, Day 10, Day 14, Day 28, Day 42, and Day 59. From these blood samples, clinical pathology parameters were monitored and the percent of CD21-positive lymphocytes (B cells) in each dog were analyzed in triplicate by FACS on PBMC isolated from whole blood using a R-phycoerythrin (RPE)-conjugated mouse anti-canine CD21 antibody (AbDserotec, cat #MCA1781 PE). The percentage of B-cells remaining at each time-point was calculated for each dog by dividing the percentage of lymphocytes that were CD21 positive at that time-point by the percentage that were CD21-positive at Day 0 (pre-dose). The averages of the percentages of B-cells remaining for each treatment group were then calculated and graphed (FIG. 6).

All antibody doses were well-tolerated in the dogs. Marked, dose-dependent decreases in the percentages of CD21-positive cells (B cells) were observed and sustained to Day 59 in beagles treated with 1, 10, or 30 mg/kg of 1E4-cIgGB. Greater than 70% depletion of B-cells was observed at Day 7 in dogs treated with either 10 or 30 mg/kg 1E4-cIgGB. CD21-positive cells remained depleted out to Day 59, with 35% and >50% suppression in animals treated with 10 or 30 mg/kg 1E4-cIgGB, respectively. Dogs that were given a single dose of either the isotype control antibody Rituxan-cIgGB (10 mg/kg) or of the lowest dose of 1E4-cIgGB (0.1 mg/kg) did not show significant changes in percentages of CD21-positive cells (B cells) during the study.

Example 4

Treatment of Dogs Having B Cell Lymphoma with the Chimeric Anti-Canine CD20 Antibody 1E4-cIgGB The 1E4 chimeric canine IgGB antibody described above is administered to Beagle male dogs having B cell lymphoma at an appropriate dose (e.g., 10 mg/kg) via intravenous bolus injection. Blood is collected from animals at various days including Day 0 (pre-dose) and, for example, Day 1, Day 2, Day 3, Day 4, Day 7, Day 10, Day 14, Day 28, Day 42, and Day 59. From these blood samples, clinical pathology parameters are monitored and the percent of CD21-positive lymphocytes (B cells) in each dog are analyzed in triplicate by FACS on PBMC isolated from whole blood using a R-phycocrythrin (RPE)-conjugated mouse anti-canine CD21 antibody (AbDserotec, cat #MCA781PE). The percentage of B-cells remaining at each time-point is calculated for each dog by dividing the percentage of CD21 positive lymphocytes at that time-point by the percentage that were CD21-positive at Day 0 (pre-dose). The averages of the percentages of B-cells remaining for each treatment group may then be calculated and graphed to confirm that the treatment is effective.

While this disclosure may have been described in terms of the preferred embodiments, it is understood that variations and modifications will occur to those skilled in the art. Therefore, it is intended that the appended claims cover all such equivalent variations that come within the scope of the invention as claimed.

What is claimed is:

1. An isolated monoclonal antibody that binds canine CD20, the antibody comprising at least one set of variable region amino acid sequences selected from the group consisting of:

a light chain variable region (LC-V) comprising the sequence of (SEQ ID NO.: 3)
DVVMTQNPLSLPVSLGDQASISCRSSQSLIYNNGNTYLHWYRQKPGQSPK

LLIYKVSNRFSGVPDRFSGSGSGTDFTLKISRVEAEDLGVYFCSQSTHVP

FTFGSGTKLEIK and a heavy chain variable region (HC-V) comprising the sequence of (SEQ ID NO.: 6)
EVQLVESGGGLVKPGGSLKLSCAASGFTFSDYGMLWVRQAPEKGLEWIAY

ISSGSSTIYYADRVKGRFTISRDNAKNTLFLQMTSLRSEDTAMYYCSTGT

FAYWGQGTPVTVSS;

an LC-V comprising the sequence of (SEQ ID NO.: 9)
DIVMTQAAPSVPVTPGESVSISCRSNKSLLHRNGNTYLYWFLQRPGQSPQ

LLIYRMSNLASGVPDRFSGSGSGTAFTLRISRVEAEDVGVYYCMQHLEFP

FTFGGGTKLEIK and a HC-V comprising the sequence of (SEQ ID NO.: 11)
EVQLQQSGPELVKPGASVKISCKASGYTFTDYYMNWVKQSHGKSLEWIGD
INPNNGDTSYNQKFKGKAPLTVDKSSSTAYMEVRSLTSEDSAVYFCARGG
VLRYPYYYVMDYWGQGTSVTVSS;

and an LC-V comprising the sequence of (SEQ ID NO.: 13)
DIVMTQSQKFMSRSVGDRVSVTCKASQNVGPNVAWYQQRPGQSPKPLIY
SASYRYSGVPDRFTGSGSGTDFTLTISNVQSEDLAEYFCQQYNNYPYTF
GGGTKLEIK and a HC-V comprising the sequence of (SEQ ID NO.: 15)
EVQLQQSGAELVRPGASVKLSCTASGFNIKDDYMHWVKQRPEQGLEWIG
WIDPENGHTKYASKFQGKATITADTSSNTAYLQLSSLTSEDTAVYYCTS
LRHYYGSSYVSPHYYWGQGTTLTVSS;

wherein the antibody binds canine CD20.

2. The monoclonal antibody of claim 1, wherein the antibody comprises at least one light chain immunoglobulin constant region amino acid sequence from canine, and at least one heavy chain immunoglobulin constant region amino acid sequence from canine.

3. The monoclonal antibody of claim 2, wherein the at least one light chain immunoglobulin constant region amino acid sequence from canine comprises at least one of the amino acid sequences selected from the group consisting of:

(SEQ ID NO.: 55)
RNDAQPAVYLFQPSPDQLHTGSASVVCLLNSFYPKDINVKWKVDGVIQD
TGIQESVTEQDKDSTYSLSSTLTMSSTEYLSHELYSCEITHKSLPSTLI
KSFQRSECQRVD, (SEQ ID NO.: 78)
RTDAQPAVYLFQPSPDQLHTGSASVVCLLNSFYPKDINVKWKVDGVIQD
TGIQESVTEQDKDSTYSLSSTLTMSSTEYLSHELYSCEITHKSLPSTLI
KSFQRSECQRVD, (SEQ ID NO.: 79)
RNDAQPAVYLFQPSPDQLHTGSASVVCLLSSFYPKDINVKWKVDGVIQD
TGIQESVTEQDKDSTYSLSSTLTMSSTEYLSHELYSCEITHKSLPSTLI
KSFQRSECQRVD,
and (SEQ ID NO.: 80)
RTDAQPAVYLFQPSPDQLHTGSASVVCLLSSFYPKDINVKWKVDGVIQD
TGIQESVTEQDKDSTYSLSSTLTMSSTEYLSHELYSCEITHKSLPSTLI
KSFQRSECQRVD;

and wherein the at least one heavy chain immunoglobulin constant region amino acid sequence from canine comprises at least one of the amino acid sequences selected from the group consisting of:

(SEQ ID NO.: 57)
ASTTAPSVFPLAPSCGSTSGSTVALACLVSGYFPEPVTVSWNSGSLTSG
VHTFPSVLQSSGLYSLSSMVTVPSSRWPSETFTCNVAHPASKTKVDKPV
PKRENGRVPRPPDCPKCPAPEMLGGPSVFIFPPKPKDTLLIARTPEVTC
VVVDLDPEDPEVQISWFVDGKQMQTAKTQPREEQFNGTYRVVSVLPIGH
QDWLKGKQFTCKVNNKALPSPIERTISKARGQAHQPSVYVLPPSREELS
KNTVSLTCLIKDFFPPDIDVEWQSNGQQEPESKYRTTPPQLDEDGSYFL
YSKLSVDKSRWQRGDTFICAVMHEALHNHYTQKSLSHSPGK, (SEQ ID NO.: 81)
ASTTAPSVFPLAPSCGSTSGSTVALACLVSGYFPEPVTVSWNSGSLTSG
VHTFPSVLQSSGLYSLSSMVTVPSSRWPSETFTCNVAHPASKTKVDKPV
PKRENGRVPRPPDCPKCPAPEPAGGPSVFIFPPKPKDTLLIARTPEVTC
VVVDLDPEDPEVQISWFVDGKQMQTAKTQPREEQFNGTYRVVSVLPIGH
QDWLKGKQFTCKVNNKALPSPIERTISKARGQAHQPSVYVLPPSREELS
KNTVSLTCLIKDFFPPDIDVEWQSNGQQEPESKYRTTPPQLDEDGSYFL
YSKLSVDKSRWQRGDTFICAVMHEALHNHYTQKSLSHSPGK, (SEQ ID NO.: 82)
ASTTAPSVFPLAPSCGSTSGSTVALACLVSGYFPEPVTVSWNSGSLTSG
VHTFPSVLQSSGLYSLSSMVTVPSSRWPSETFTCNVAHPASKTKVDKPV
PKRENGRVPRPPDCPKCPAPEMLGGPSVFIFPPKPKDTLLIARTPEVTC
VVVDLDPEDPEVQISWFVDGKQMQTAKTQPREEQFAGTYRVVSVLPIGH
QDWLKGKQFTCKVNNKALPSPIERTISKARGQAHQPSVYVLPPSREELS
KNTVSLTCLIKDFFPPDIDVEWQSNGQQEPESKYRTTPPQLDEDGSYFL
YSKLSVDKSRWQRGDTFICAVMHEALHNHYTQKSLSHSPGK,
and (SEQ ID NO.: 83)
ASTTAPSVFPLAPSCGSTSGSTVALACLVSGYFPEPVTVSWNSGSLTSG
VHTFPSVLQSSGLYSLSSMVTVPSSRWPSETFTCNVAHPASKTKVDKPV
PKRENGRVPRPPDCPKCPAPEAAGGPSVFIFPPKPKDTLLIARTPEVTC
VVVDLDPEDPEVQISWFVDGKQMQTAKTQPREEQFNGTYRVVSVLPIGH
QDWLKGKQFTCKVNNKALPSPIERTISKARGQAHQPSVYVLPPSREELS
KNTVSLTCLIKDFFPPDIDVEWQSNGQQEPESKYRTTPPQLDEDGSYFL
YSKLSVDKSRWQRGDTFICAVMHEALHNHYTQKSLSHSPGK.

4. A method for treating a canine CD20-expressing lymphoma in a canine animal comprising administering to the animal at least one effective dose of the monoclonal antibody of claim 1.

5. The method of claim 4 wherein the monoclonal antibody is administered in a dosage amount of about 1 to 50 mg/kg of body weight of the animal.

6. The method of claim 4 wherein multiple doses are administered to the animal.

7. The method of claim 4 wherein the monoclonal antibody is administered in conjunction with one or more chemotherapeutic agents.

* * * * *

UNITED STATES PATENT AND TRADEMARK OFFICE
CERTIFICATE OF CORRECTION

PATENT NO.         : 9,790,280 B2
APPLICATION NO.    : 14/354280
DATED              : October 17, 2017
INVENTOR(S)        : Sarah Rue et al.

It is certified that error appears in the above-identified patent and that said Letters Patent is hereby corrected as shown below:

On the Title Page

Column 2 item (56), under (Other Publications), Line 6: Please delete "humanzied" and insert -- humanized --, therefor.

Signed and Sealed this
Twenty-second Day of May, 2018

Andrei Iancu
*Director of the United States Patent and Trademark Office*